(12) United States Patent
Murray

(10) Patent No.: US 11,612,418 B2
(45) Date of Patent: Mar. 28, 2023

(54) REVISION CONNECTORS, SYSTEMS, AND METHODS THEREOF

(71) Applicant: GLOBUS MEDICAL, INC., Audubon, PA (US)

(72) Inventor: Patrick Murray, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/713,074

(22) Filed: Dec. 13, 2019

(65) Prior Publication Data
US 2021/0177468 A1   Jun. 17, 2021

(51) Int. Cl.
A61B 17/70   (2006.01)

(52) U.S. Cl.
CPC ...... A61B 17/7049 (2013.01); A61B 17/7032 (2013.01)

(58) Field of Classification Search
CPC ............ A61B 17/7052; A61B 17/7049; A61B 17/7043; A61B 17/705
See application file for complete search history.

(56) References Cited

U.S. PATENT DOCUMENTS

| | | | |
|---|---|---|---|
| 6,234,705 B1 | 5/2001 | Troxell | |
| 6,283,967 B1 | 9/2001 | Troxell et al. | |
| 6,306,137 B2 | 10/2001 | Troxell | |
| 6,554,832 B2 | 4/2003 | Shluzas | |
| 7,717,940 B2 | 5/2010 | Woods et al. | |
| 7,744,633 B2 | 6/2010 | Berrevoets et al. | |
| 7,927,355 B2 | 4/2011 | Berrevoets et al. | |
| 8,361,117 B2 | 1/2013 | Michielli et al. | |
| 8,430,916 B1* | 4/2013 | Winslow ............ | A61B 17/7007 606/250 |
| 8,758,411 B1 | 6/2014 | Rayon et al. | |
| 8,828,055 B2 | 9/2014 | Blain et al. | |
| 8,870,921 B2 | 10/2014 | Michielli et al. | |
| 9,107,703 B2 | 8/2015 | Torres | |
| 9,131,964 B2 | 9/2015 | Blain et al. | |
| 9,381,044 B2 | 7/2016 | Robinson et al. | |
| 9,451,994 B1 | 9/2016 | Whipple et al. | |
| 9,468,469 B2 | 10/2016 | Otte et al. | |
| 9,468,471 B2 | 10/2016 | Otte et al. | |
| 9,517,089 B1* | 12/2016 | Casey ............... | A61B 17/7035 |
| 9,572,601 B2 | 2/2017 | Stenulson et al. | |
| 9,668,779 B2 | 6/2017 | Okamoto | |
| 9,949,768 B2 | 4/2018 | Rathbun et al. | |
| 10,251,678 B2 | 4/2019 | Alsup et al. | |
| 10,271,878 B2 | 4/2019 | Courtney et al. | |
| 10,357,290 B2 | 4/2019 | Torres | |
| 2006/0064090 A1* | 3/2006 | Park .................. | A61B 17/7005 606/259 |

(Continued)

FOREIGN PATENT DOCUMENTS

| | | |
|---|---|---|
| EP | 1459690 A1 | 9/2004 |
| WO | 2019117251 A1 | 6/2019 |

OTHER PUBLICATIONS

"RELINE Technique Guide", NUVASIVE, Mar. 2009, pp. 1-23.

*Primary Examiner* — Julianna N Harvey

(57) ABSTRACT

Connector assemblies, systems, and methods thereof. One or more modular connectors has a first portion that clamps to a first rod in an existing construct and a second portion that clamps to a second rod in a new construct such that the new construct can be extended from the existing construct.

10 Claims, 17 Drawing Sheets

(56) References Cited

U.S. PATENT DOCUMENTS

| | | | |
|---|---|---|---|
| 2006/0079892 A1* | 4/2006 | Roychowdhury | A61B 17/7044 606/253 |
| 2012/0232593 A1 | 9/2012 | Predick | |
| 2018/0280062 A1 | 10/2018 | Lee et al. | |
| 2018/0280063 A1* | 10/2018 | Lee | A61B 17/7052 |
| 2020/0229848 A1* | 7/2020 | Palagi | A61B 17/7052 |

* cited by examiner

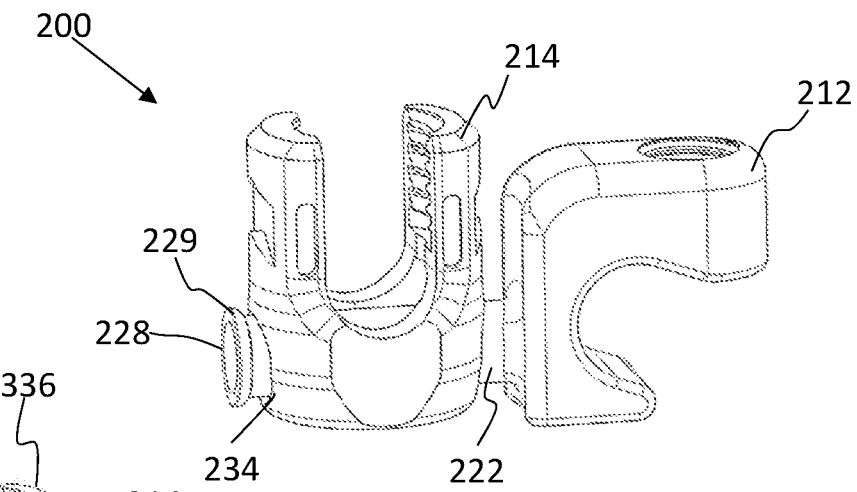
FIG. 7
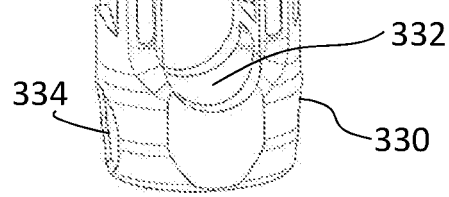
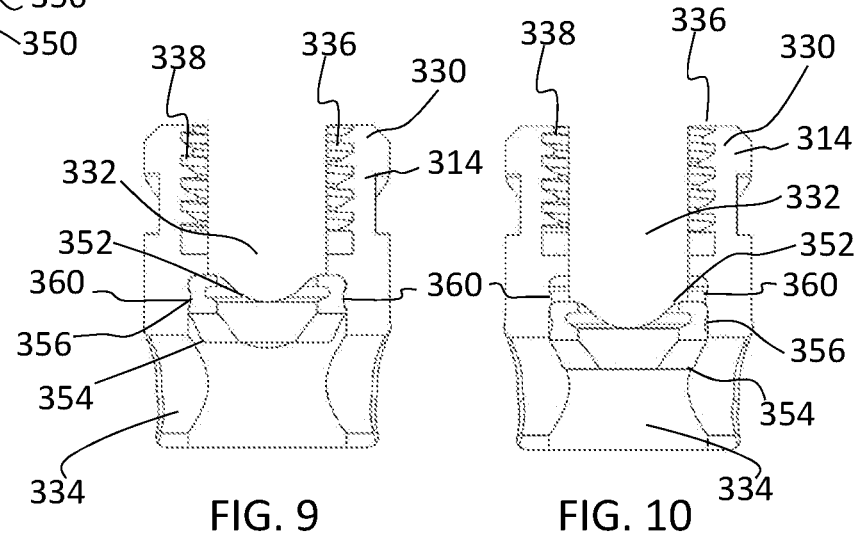
FIG. 8
FIG. 9
FIG. 10

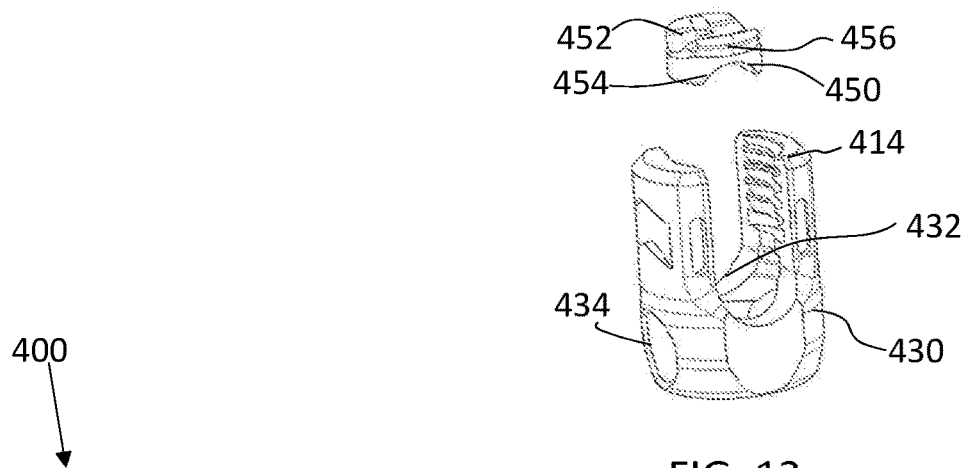
FIG. 13
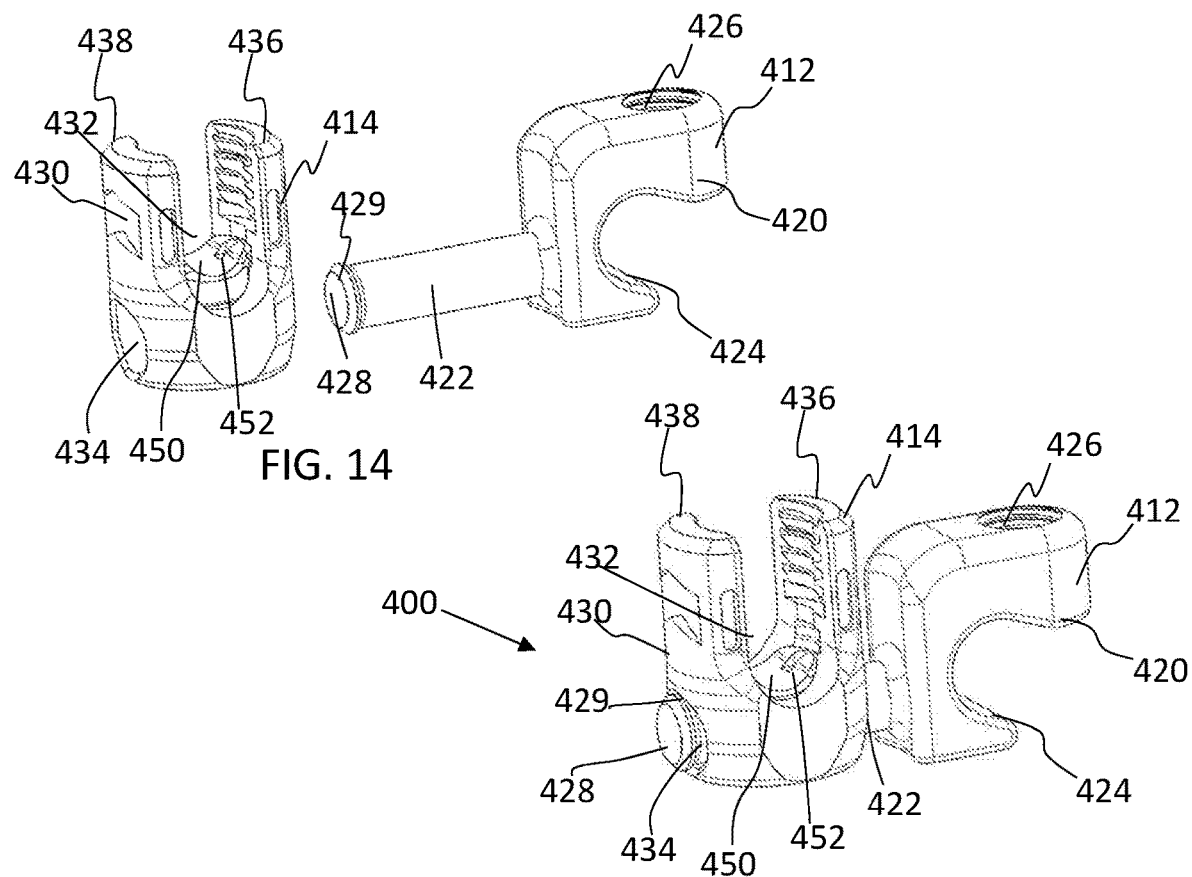
FIG. 14
FIG. 15

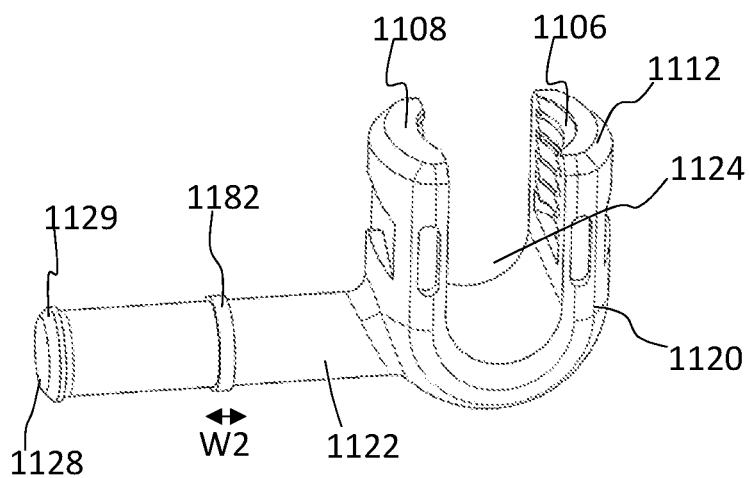
FIG. 36
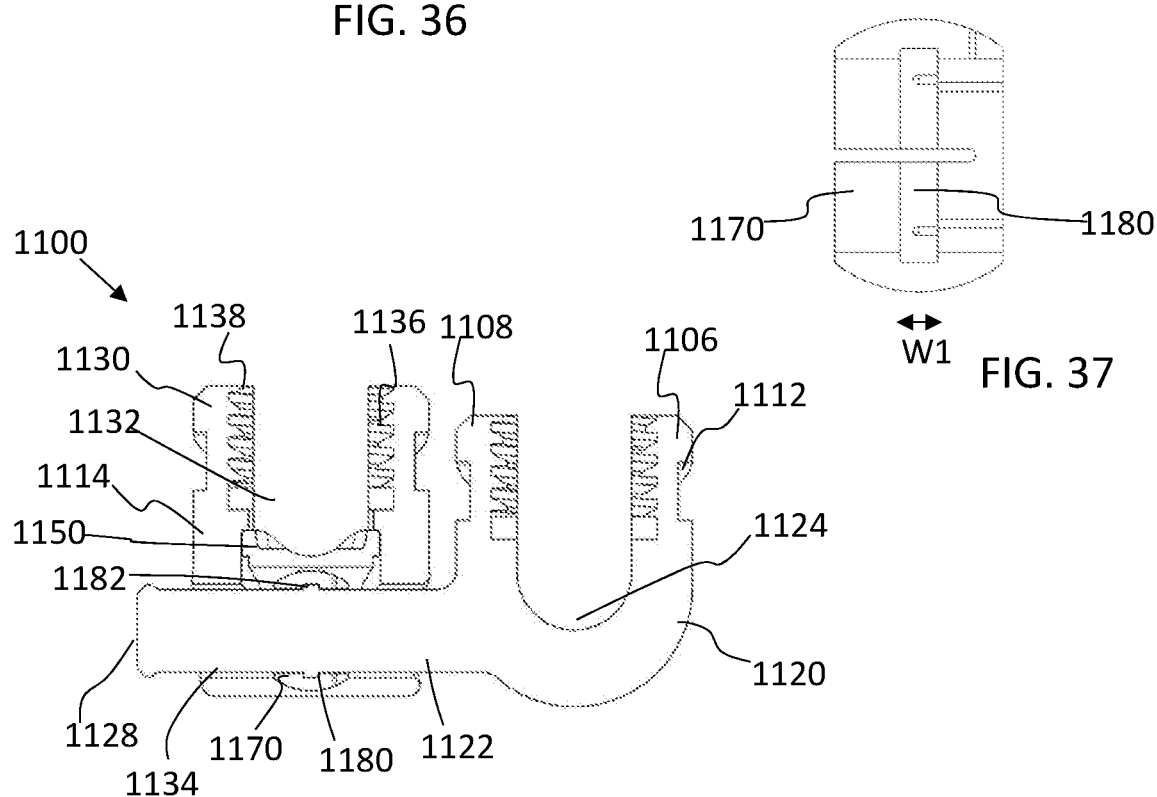
FIG. 37
FIG. 38

REVISION CONNECTORS, SYSTEMS, AND METHODS THEREOF

FIELD OF THE INVENTION

The present disclosure relates to surgical devices, and more particularly, to rod connectors, such as spinal hardware connectors for revision surgeries.

BACKGROUND OF THE INVENTION

At times, spinal surgeons may need to add additional fixation to spinal segments adjacent to previously instrumented levels. In these cases, the hardware from the initial surgery may interfere with placement of new fixation for the adjacent level. Therefore, there is a need for connector implants that attach to the existing spinal fusion construct on one end and extend fixation to one or more adjacent levels in need of fusion. Quicker recovery times and lessened discomfort may make minimally invasive surgical (MIS) techniques favorable in these situations.

SUMMARY OF THE INVENTION

In accordance with the application, in some embodiments, components, systems, and methods for connecting one device to another are provided. For example, one elongate implant, such as a first rod, may be coupled to another elongate implant, such as a second rod. The elongate implants, such as spinal rods, are well known to connect adjacent vertebrae in a spinal fusion procedure. Depending on the configuration of rods or implants, it may be desirable to have one rod connected to another rod or additional implant. In the case of two or more rods, these rods may be interconnected with one or more connectors, for example, in a single given surgery, such as a scoliosis operation, or at a later surgery, for example, in a revision surgery.

In a revision surgery, connectors can be used to connect new fixation constructs to existing fixation constructs without the need to remove the original hardware. The hardware from the index surgery oftentimes interferes with placement of new fixation for the adjacent level. Differences in screw trajectory and location between the existing construct and the new pedicle screws can make connecting the two segments difficult. Therefore, it is advantageous for connector implants to be able to translate and/or rotate in order to accommodate these differences. The spinal connector implants may offer the ability to translate and/or rotate in order to ease the connection between existing constructs and adjacent level(s) in revision surgeries. The different connection modes provided in the following exemplary embodiments offer a range of options to be chosen based on a specific clinical scenario and/or surgeon preference. Although certain configurations are shown herein, it is envisioned that any suitable number, type, and selection of connectors and implants may be chosen and configured by the skilled surgeon.

According to one embodiment, an implant or connector system includes a first attachment portion and a second attachment portion. The first attachment portion has a first body portion configured to receive and secure a first spinal rod. The first attachment portion has a longitudinal member extending from the first body portion and terminating at a free end. The second attachment portion has a second body portion configured to receive and secure a second spinal rod. The second attachment portion has an opening extending therethrough. The longitudinal member of the first attachment portion is received through the opening of the second attachment portion. The second attachment portion is able to translate along the longitudinal member (e.g., adjusting the length or distance between the first and second attachment portions) and/or rotate about the longitudinal member of the first attachment portion (e.g., adjusting the angle between the first and second attachment portions).

In some embodiments, the connector systems may include one or more of the following features. The longitudinal member of the first attachment portion may define an elongate slot where a pin is receivable through the elongate slot and into an opening in the second attachment portion to thereby secure the second attachment portion to the first attachment portion. The free end of the longitudinal member may be enlarged (e.g., by peening) such that the second attachment portion is unable to be disassembled from the first attachment portion. The second attachment portion may include a saddle (e.g., bottom loaded or top loaded) having an upper surface configured to contact the second spinal rod and a lower surface configured to contact the longitudinal member of the first attachment portion. The internal cavity of the second body portion may define at least one bump, wherein when the saddle is positioned above the bump, the saddle is in an assembly position, in which the longitudinal member of the first attachment portion can be inserted through the opening of the second attachment portion until the free end of the longitudinal member exits the opening. When the saddle is positioned below the bump, the longitudinal member is prevent from being removed from the second attachment portion due to the larger size of the free end of the longitudinal member relative to the diameter of the opening once the saddle is positioned below the bump.

The saddle may include a first grooved surface on the lower surface configured to mate with a second grooved surface on the longitudinal member. The first attachment portion may be side loaded, bottom loaded, top loaded, open, closed, or tulip-style, for example.

According to one embodiment, a connector system includes a first attachment portion, a second attachment portion, a ball joint, and a saddle. The first attachment portion has a first body portion configured to receive and secure a first spinal rod. The first attachment portion has a longitudinal member extending from the first body portion and terminating at a free end. The second attachment portion has a second body portion configured to receive and secure a second spinal rod. The second attachment portion has an opening extending therethrough. The ball joint may be receivable within the opening of the second attachment portion or inserted into the second attachment portion through the same opening that receives the second spinal rod (i.e., inserted in the same manner as the saddle). The saddle has an upper surface configured to receive a portion of the second spinal rod and a lower surface configured to contact the ball joint. The longitudinal member of the first attachment portion is receivable through the ball joint. The second attachment portion is able to translate, rotate, wag, and/or tilt about the longitudinal member of the first attachment portion.

In some embodiments, the connector system may include one or more of the following features. The ball joint may have a spherical outer surface. The ball joint may define a plurality of slits configured to expand and contract about the longitudinal member. The longitudinal member may include a mating ring, and the ball joint may define a slot configured to accept the mating ring. A width of the slot in the ball joint may be greater than a width of the mating ring, thereby allowing for translation of the second attachment portion along the longitudinal member. A spherical recess within the second body portion may be larger than an overall size of the ball joint, thereby allowing for translation of the ball joint within the second body portion of the second attachment portion. The first attachment portion may include a second saddle having a groove and a pin receivable within the groove such that the second saddle is able to rotate about a vertical axis of the first attachment portion.

According to another embodiment, a revision system includes a first spinal rod, a second spinal rod, a first attachment portion and a second attachment portion. The first attachment portion has a first body portion configured to receive and secure the first spinal rod. The first attachment portion has a longitudinal member extending from the first body portion and terminating at a free end. The second attachment portion has a second body portion configured to receive and secure the second spinal rod. The second attachment portion has an opening extending therethrough. The ball joint is receivable within the opening of the second attachment portion or inserted into the second attachment portion through the same opening that receives the second spinal rod (i.e., inserted in the same manner as the saddle). The saddle has an upper surface configured to receive a portion of the second spinal rod and a lower surface configured to contact the ball joint. The longitudinal member of the first attachment portion is receivable through the ball joint. The second attachment portion is able to translate, rotate, wag, and/or tilt about the longitudinal member of the first attachment portion. When a locking member is secured to the second attachment portion, a downward force is applied to the saddle, which applies a force to the ball joint, thereby locking the position of the second attachment portion relative to the first attachment portion. One of the first or second spinal rods may be an existing spinal rod previously implanted in a patient, and the other of the first or second spinal rods may be a new spinal rod being implanted in a revision procedure.

According to yet another embodiment, a method of revising an existing construct includes providing a first spinal rod previously implanted into a patient, providing a second spinal rod for use in the revision procedure, and implanting a connector to attach the second spinal rod to the first spinal rod. The first attachment portion of the connector is attached to the first spinal rod. The second attachment portion is translated linearly along the length of the longitudinal member and/or the second attachment portion is rotated about the longitudinal member. Once the desired distance and angle is achieved, the second attachment portion is secured to the second spinal rod.

Also provided are kits including connectors of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 7 shows a perspective view of a connector according to one embodiment having a distal end of the longitudinal member configured to prevent disassembly of the first attachment portion from the second attachment portion;

FIG. 8 is an exploded perspective view of a second attachment portion according to another embodiment having a modular saddle component loaded from the bottom;

FIG. 9 is a cross-sectional view of the second attachment portion of FIG. 8 with the saddle component in an upward position;

FIG. 10 is a cross-sectional view of the second attachment portion of FIG. 8 with the saddle component in a downward position;

FIG. 13 is an exploded perspective view of a second attachment portion according to another embodiment having a modular saddle component loaded from the top;

FIG. 14 is an exploded perspective view of the first and second attachment portions with the modular saddle component of FIG. 13 in the upward position such that the first and second attachment portion are able to move relative to one another;

FIG. 15 shows a perspective view of the first and second attachment portion with the modular saddle component of FIG. 13 in the downward position such that the first and second attachment portions are locked together;

FIG. 36 is a perspective view of a first attachment portion according to another embodiment having a ring on the longitudinal member;

FIG. 37 is a cross-section view of a spherical joint component according to another embodiment;

FIG. 38 is a cross-sectional view of a connector having the first attachment portion of FIG. 36 and the spherical joint component of FIG. 37;

DETAILED DESCRIPTION OF THE INVENTION

Embodiments of the present application are generally directed to components, systems, and methods for connecting one elongate implant, such as a first rod, to another elongate implant, such as a second rod. The elongate implants, such as spinal rods, are well known to connect adjacent vertebrae in a spinal fusion procedure. Depending on the configuration of rods or implants, it may be desirable to have one rod connected to another rod or additional implant. In the case of two or more rods, these rods may be interconnected with one or more connectors, for example, in a single given surgery, such as a scoliosis operation, or at a later surgery, for example, in a revision surgery.

For example, connectors can be used to connect new fixation constructs to existing fixation constructs without the need to remove index surgery hardware. One or more benefits to such direct attachment to existing constructs saves operating time, causes less disruption to the patient, and minimizes patient healing time. The ability of the connectors to maintain connection with existing constructs can maximize utility in cases of varying patient anatomy and existing spinal constructs. The different connection modes provided in the following exemplary embodiments offer a range of options to be chosen based on a specific clinical scenario and/or surgeon preference. Thus, although certain configurations are shown herein, it is envisioned that any suitable number, type, and selection of connectors and implants, such as rods, may be chosen and configured by the skilled surgeon.

While the different connection modes disclosed herein can be used independently, those skilled in the art will recognize that the connection modes can be combined as needed according to patient needs. Further, while the connection modes disclosed herein can be provided separately, kits that include various and multiple combinations of different connection modes can also be provided.

Figure 1:
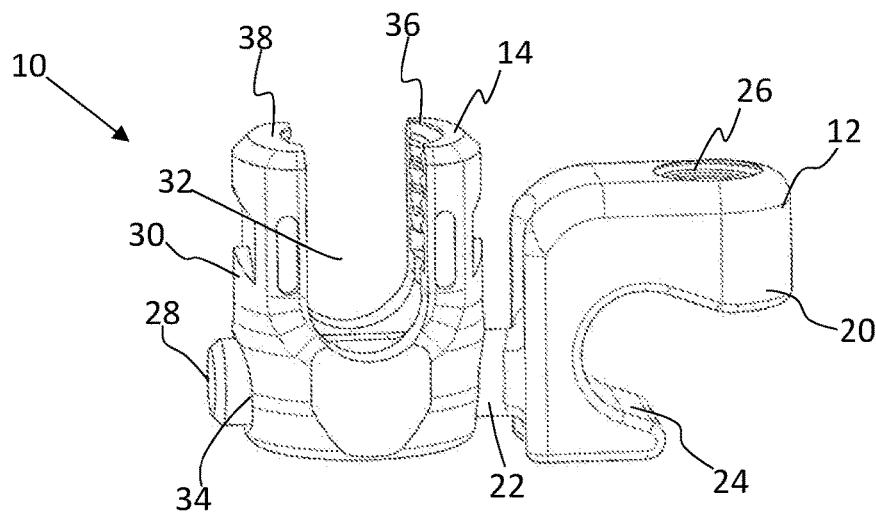
FIG. 1 is a perspective view of a connector according to one embodiment with a first attachment portion for attachment onto a first spinal rod and a second attachment portion for attachment onto a second spinal rod.
Figure 2:
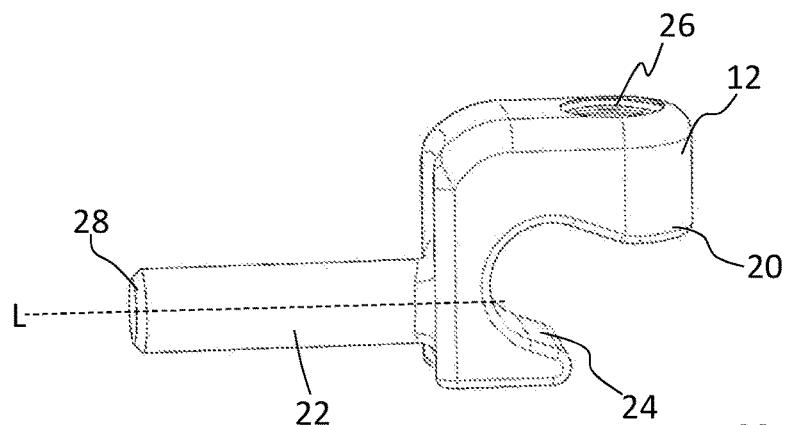
FIG. 2 is a perspective view of the first attachment portion of FIG. 1 including a longitudinal member.
Figure 3:
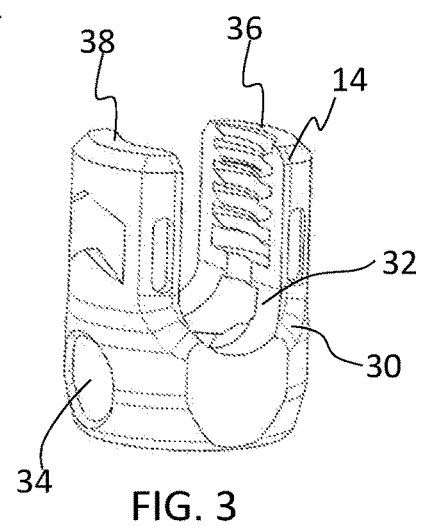
FIG. 3 is a perspective view of the second attachment portion of FIG. 1 having a tulip configuration.
Figure 22:
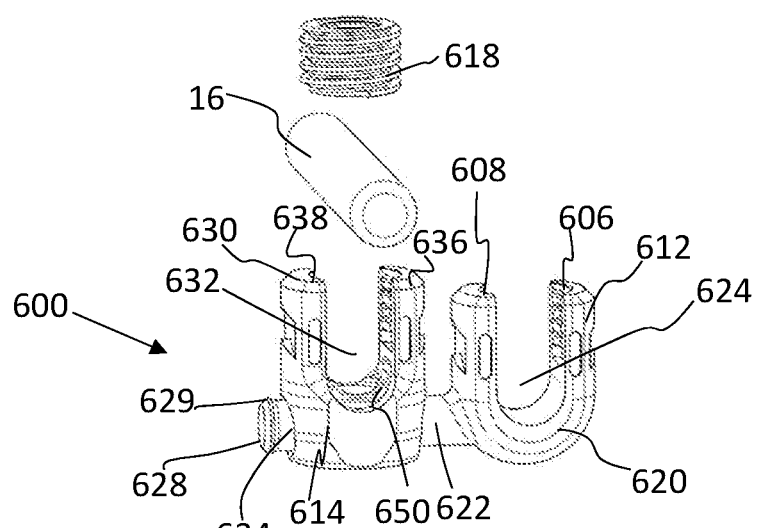
FIG. 22 shows an exploded view of a connector, a spinal rod, and a locking cap.
Figure 23:
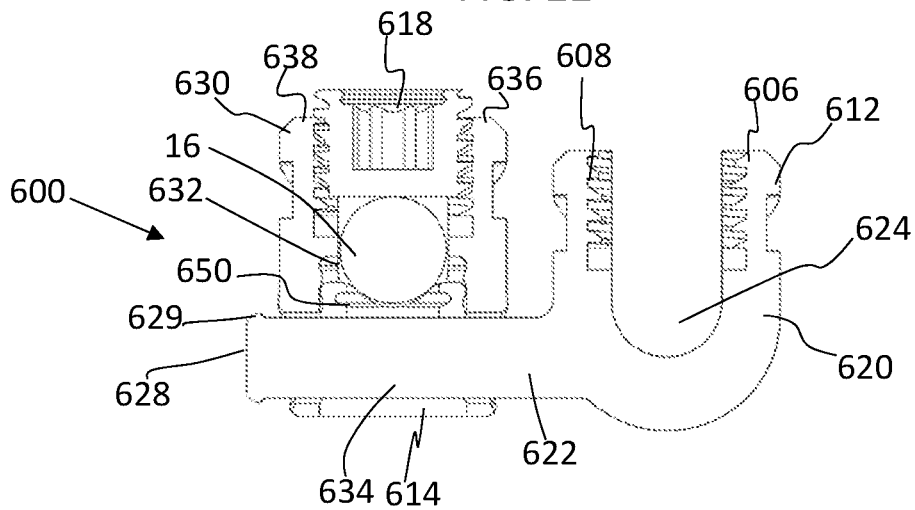
FIG. 23 is a cross-sectional view of the connector of FIG. 22 with the locking cap securing the spinal rod and saddle, and thereby locking the construct.

Referring now to FIG. 1-3, an implant, connector assembly, or connector 10 according to one embodiment is shown. The connector 10 includes a first attachment portion 12 and a second attachment portion 14. The first attachment portion 12 is configured for attachment onto a first elongate implant, such as a spinal rod 16 (shown in FIG. 17) and the second attachment portion 14 is configured for attachment onto a second elongate implant, such as a spinal rod 16 (shown in FIG. 22). The two attachment portions 12, 14 are able to rotate and/or translate with respect to one another. In other words, the second attachment portion 14 is able to rotate relative to the first attachment portion 12 such that an angle between the first and second rods 16 may be adjusted, and/or the second attachment portion 14 is able to translate relative to the first attachment portion 12 such that a distance between the first and second attachment portions 12, 14 may be adjusted.

Figure 16:
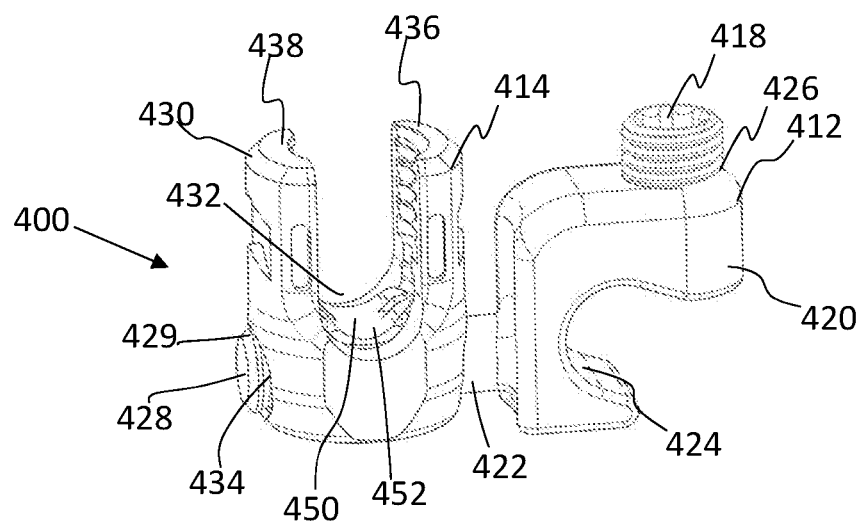
FIG. 16 shows a perspective view of a connector according to one embodiment having an open style clamp.
Figure 17:
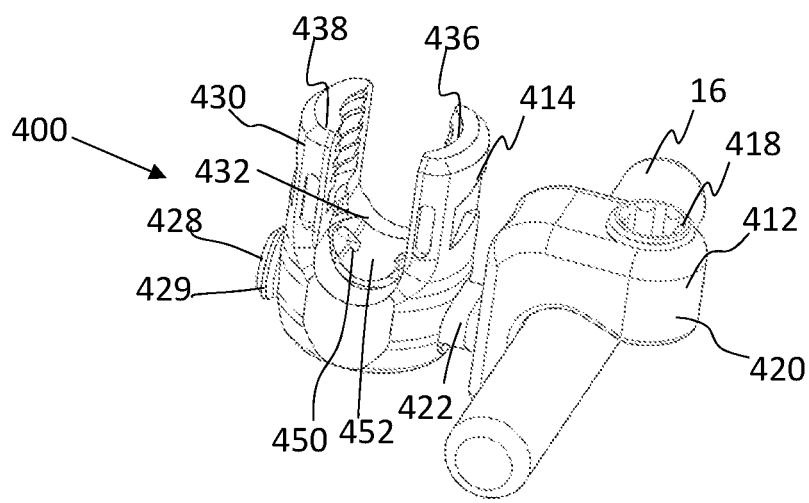
FIG. 17 shows the connector of FIG. 16 secured to a spinal rod.

As best seen in FIG. 2, the first attachment portion 12 has a first body portion or body 20 with a longitudinal member 22 extending from the body 20. The body 20 of the first attachment portion 12 defines an opening 24 in the form or an arcuate recess configured to receive the first elongate member, such as the first spinal rod 16. The arcuate recess 24 allows for the rod 16 to be side loaded and/or bottom loaded into the body 20 of the first attachment portion 12. The body 20 defines a through hole or opening 26 extending from an upper surface of the body 20 and in fluid communication with the opening 24. When a locking cap or securing member, such as a threaded cap 418 shown in FIG. 16, is positioned within the opening 26, rod 16 positioned within recess 24 is secured or locked into position (as shown in FIG. 17). Embodiments of connectors having a rod secured by a securing member, such as a threaded locking cap, are described in more detail in U.S. Publication No. 2019/0321083, which is incorporated by reference herein in its entirety for all purposes.

The longitudinal member 22 of the first attachment portion 12 may terminate as a free end 28 at its distal-most tip. The longitudinal member 22 may extend along a central longitudinal axis L. The central longitudinal axis L may be generally aligned with the opening 24 for the first rod 16. Although it is envisioned that the longitudinal member 22 may be otherwise positioned from the body 20 of the first attachment portion, the connector 10 may be configured as a low-profile connector. The longitudinal member 22 may be generally cylindrical in shape or of another suitable cross-section. The longitudinal member 22 may have a generally uniform dimension (e.g., diameter) or may vary along its length.

As best seen in FIG. 3, the second attachment portion 14 has a second body portion or body 30 with a head style clamp, generally u-shaped, or tulip-type configuration. The body 30 may include a first extension 36 separated by a second extension 38, thereby defining a generally tulip-style connector. The second body 30 defines an opening 32 in the form of a u-shaped recess between the first and second extensions 36, 38, and the bottom surface of the arcuate recess 32 is configured to receive the second elongate member, such as the second spinal rod 16. The recess 32 allows for the rod 16 to be top loaded into the body 30 of the second attachment portion 14.

The second body 30 defines a second cavity or thru hole 34 configured to accept the longitudinal member 22 of the first attachment portion 12. The first recess 32 may be in fluid communication with hole 34, and the hole 34 may extend generally transverse and/or perpendicular to the first opening 32. In some embodiments, the hole 34 is a through hole extending from a first side of the second body to a second side opposite the first side. In some embodiments, the hole 34 may alternatively be a blind hole that extends from the first side of the second body 30 and terminates at a point between the first side and the second side. One or more inner surfaces of the first and second extensions 36, 38 may be threaded or otherwise configured to engage with a securing member or locking cap, such as a threaded cap 618, shown in FIG. 22. One or more outer surfaces of the first and second extensions 36, 38 may include one or more indentations or other features configured to engage with an instrument for installing the connector 10.

The second attachment portion 14 is able to translate along and/or rotate about the longitudinal member 22 of the first attachment portion 12. The second attachment portion 14 is able to rotate relative to longitudinal axis L of the longitudinal member 22 such that an angle between the first and second rods 16 may be adjusted. The second attachment portion 14 is able to linearly translate along the longitudinal member 22 such that a distance between the first and second attachment portions 12, 14 and correspondingly a distance between the first and second rods 16 may be adjusted.

The implant 10 is assembled such that the second attachment portion 14 is retained on the longitudinal member 22 extending from the first attachment portion 12. In an unlocked position, the second attachment portion 14 is able to translate along the longitudinal member 22 along the longitudinal axis L and/or the second attachment portion 14 is able to rotate about the longitudinal member 22 around the longitudinal axis L. The second attachment portion 14 may be locked by positioning a locking cap or securing member, such as a threaded cap 618, into the top of the opening 32, thereby pressing against the rod 16 which presses against the longitudinal member 22, which in turn presses against a saddle (not shown in FIGS. 1-3) that presses down and locks the longitudinal member 22 within the second attachment portion 14. Thus, in a locked position, the location and orientation of the second attachment portion 14 is fixed relative to the first attachment portion 12, thereby securing the location and position of the first and second rods 16.

Figure 4:
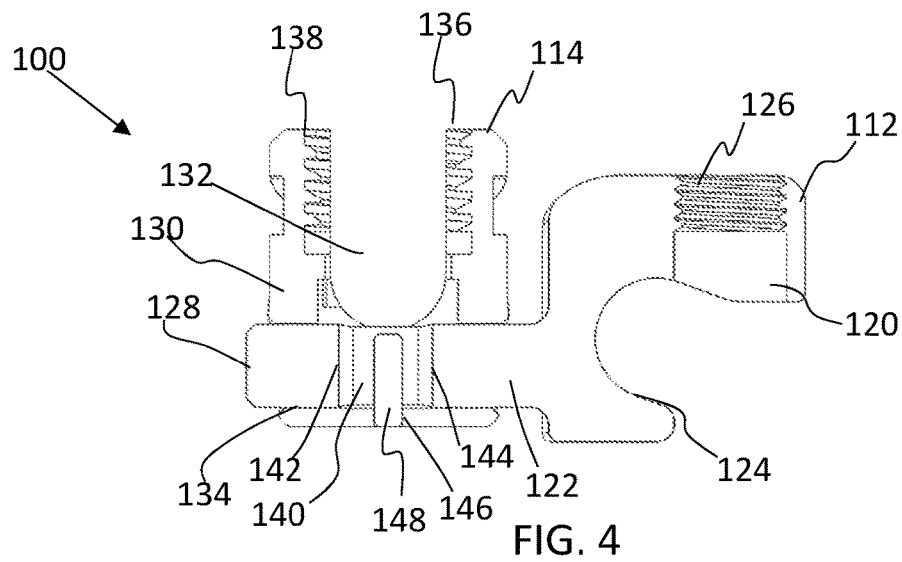
FIG. 4 is a cross-sectional view of a connector according to one embodiment having a pin and slot configuration.
Figure 5:
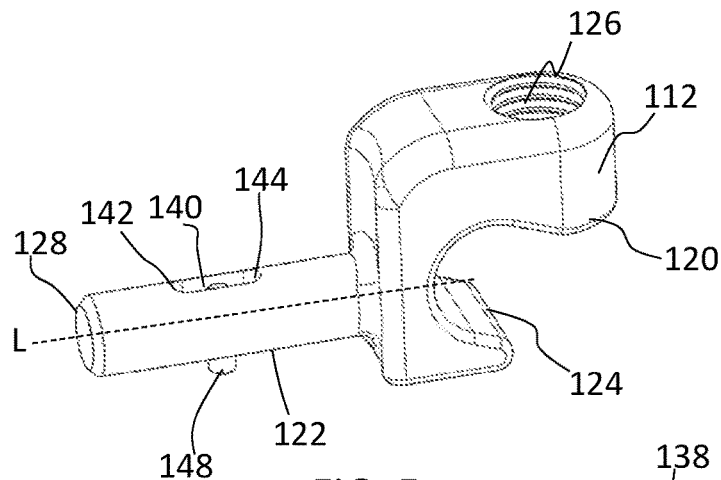
FIG. 5 is a perspective view of the first attachment portion of FIG. 4 having a slot configurated to accept the pin.
Figure 6:
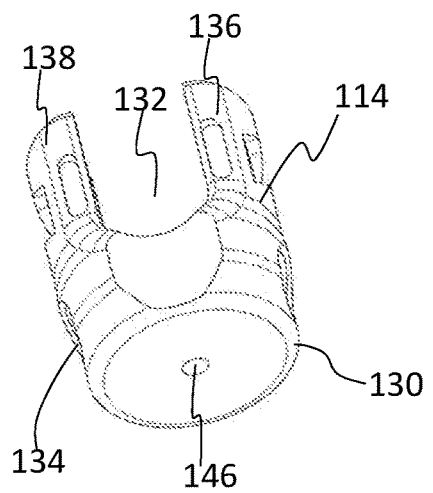
FIG. 6 is a perspective view of the second attachment portion of FIG. 4 having a connection hole configured to accept the pin.

Turning now to FIGS. 4-6, an implant, connector assembly, or connector 100 according to one embodiment is shown. Connector 100 is similar to connector 10 except that a pin 148 and slot 140 are provided to connect the second attachment portion 114 to the first attachment portion 112. Similar to connector 10, connector 100 includes a first attachment portion 112 with a body 120 having a recess 124 for receiving first rod 16 and an opening 126 for receiving a securing member, such as a threaded cap 418 (shown in FIG. 17), to secure the rod 16. The longitudinal member 122 extends to a free end 128, which is positioned within opening 134 in the body 130 of the second attachment portion 114. In some embodiments, the opening 134 is a through hole extending from a first side of the second body to a second side opposite the first side. In some embodiments, the opening 134 may alternatively be a blind hole that extends from the first side of the second body 30 and terminates at a point between the first side and the second side. The second attachment portion 114 has a tulip shaped body 130 with first and second extensions 136, 138 separated by an opening 132 configured to receive second rod 16.

In this embodiment, the first attachment portion 112 includes a longitudinal member 122 having a slot 140 extending therethrough. The slot 140 may extend from an upper portion of the longitudinal member 122 to a lower portion of the longitudinal member 122. The slot 140 may be elongated along the longitudinal axis L. The slot 140 may extend from a first end 142 to a second end 144 along the length of the longitudinal member 122. The second attachment portion 114 has a thru hole 146 in its bottom surface. A pin 148 is passed through the hole 146 in the second attachment portion 114 and into the slot 140 in the longitudinal member 122 of the first attachment portion 114, thereby retaining the two attachment portions 112, 114 together. The pin 148 and slot 140 configuration allow for the second attachment portion 114 to translate along the length of the slot 140 in the longitudinal member 122 of the first attachment portion 112. The total amount of translation is controlled by the length of the slot 140 between the first and second ends 142, 144. The pin 148 may be held rigidly within the opening 146 of the second attachment portion 114, for example, with a press fit tolerance, weld, adhesive, or other suitable secure fixation.

Turning now to FIG. 7, an embodiment of a connector 200, similar to connector 10 is shown, where the longitudinal member 222 of the first attachment portion 212 includes an enlarged distal end 229 configured to secure the second attachment portion 214 to the first attachment portion 212 when assembled. The longitudinal member 222 of the first attachment portion 212 is passed through the thru hole 234 of the second attachment portion 214. The free end 228 of the longitudinal member 222 is then peened or otherwise deformed such that the circumference of the distal portion 229 grows enough to retain the second attachment portion 214 on the longitudinal member 222 of the first attachment portion 212. In other words, the enlarged distal portion 229 has a diameter greater than a diameter of the opening 234 through the second attachment portion 214 such that the second attachment portion 214 is unable to slide past the free end 228 of the longitudinal member 222, thereby preventing disassembly.

In an alternative configuration, the enlarged distal portion 229 is an end cap that can be threaded onto free end 228 of the longitudinal member 222. The longitudinal member 222 of the first attachment portion 212 is passed through the thru hole 234 of the second attachment portion 214. The end 228 of the longitudinal member 222 has a thread which can mate with a corresponding thread within an end cap component 229. The size of the end cap 229 is enlarged such that it cannot pass through the thru hole 234 of the second attachment portion 214. The end cap component 229 may be threaded onto the longitudinal member 222 of the first attachment portion 212 in order to retain the second attachment portion 214 on the longitudinal member 222 of the first attachment portion 212.

In another alternative configuration, the enlarged distal portion 229 is an end cap that can be press-fit onto the end 228 of the longitudinal member 222. The longitudinal member 222 of the first attachment portion 212 is passed through the thru hole 234 of the second attachment portion. The end 228 of the longitudinal member 222 has a geometry such that the end cap component 229 can be pressed onto it. The size of the end cap 229 is such that it cannot pass through the thru hole 234 of the second attachment portion 214. The end cap component 229 may be press-fit onto the longitudinal member 222 of the first attachment portion 212 in order to retain the second attachment portion 214 on the longitudinal member 222 of the first attachment portion 212. Although peened, threaded end caps, and press-fit end caps are exemplified, it may be envisioned that other suitable arrangements may be used to prevent the second attachment portion 214 from separating from the first attachment portion 212 while still allowing for translation and/or rotation of the two components in use. In some embodiments, the hole 234 may alternatively be a blind hole.

With emphasis on FIGS. 8-12, an embodiment of an implant, connector assembly, or connector 300 is shown. Connector 300 is similar to connector 10 but the second attachment portion 314 further includes a bottom loaded modular saddle 350. Similar to connector 10, connector 300 includes a first attachment portion 312 with a body 320 having a recess 324 for receiving rod 16 and an opening 326 for receiving a securing member, such as a threaded cap 418 (shown in FIG. 17), to secure the rod 16. The longitudinal member 322 extends to a free end 328, which is positioned within opening 334 in the body 330 of the second attachment portion 314. The second attachment portion 314 has a tulip shaped body 330 with first and second extensions 336, 338 separated by an opening 332 configured to receive rod 16. Similar to connector 200, the end 328 of the longitudinal member 322 may be an enlarged end 329.

The second attachment portion 314 includes saddle component 350, which is configured to be loaded in from the bottom of the second attachment portion 314. The saddle 350 includes an upper surface defining a first slot 352 for receiving a portion of rod 16 and a lower surface defining a second slot 354 for receiving a portion of the longitudinal member 322. The first slot 352 may define a contoured or curved slot which matches the outer shape of the rod 16, and the second slot 354 may define a contoured or curved slot which matches the outer shape of the longitudinal member 322. The saddle 350 defines a recess or groove 356 along an outer surface of the saddle 350. The saddle 350 may be elliptical in shape to keep the rod slot 352 oriented with the rod slot 332 of the second attachment portion 350 and the bottom slot 354 oriented with the thru hole 334 of the second attachment portion 350 configured to accept the longitudinal member 322.

Figure 11:
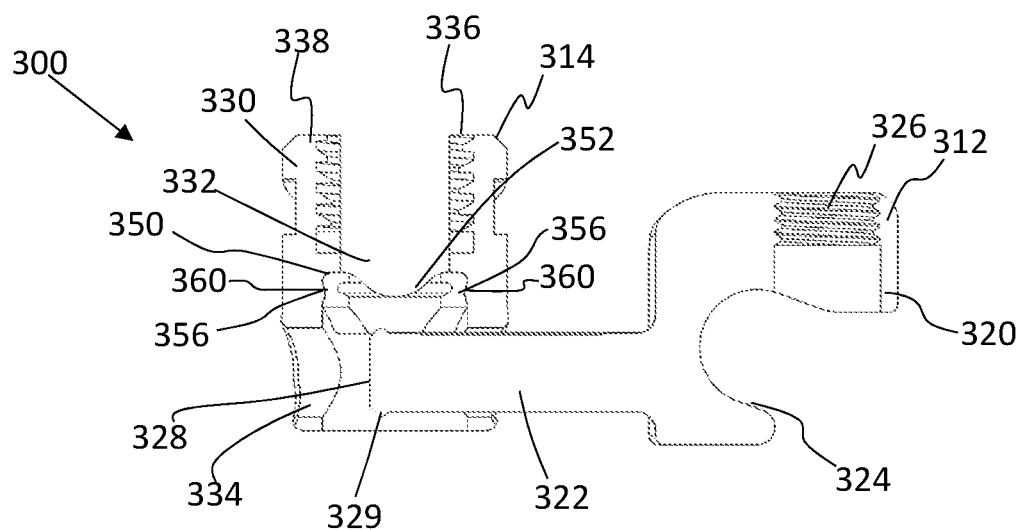
FIG. 11 shows a cross-sectional view of the longitudinal member passing under the saddle component in the upward position.

The saddle 350 may be loaded straight in from the bottom in the correct orientation. The inner geometry of the second attachment portion 314 is such that the saddle 350 may exist in two locations—above a modular bump 360 (best seen in FIG. 9) and below the modular bump 360 (best seen in FIG. 10). The bump 360 may be configured to engage with the groove 356. The bump 360 may be a single bump or protrusion, a plurality of bumps or protrusions, or a continuous ring around the inner cavity of the second attachment portion 314. The saddle 350 is able to be forcibly moved between at least two locations. As best seen in FIGS. 9 and 11, the geometry of the second attachment portion 314 is such that when the saddle 350 is located above the modular bump 360 and/or the bump 360 is engaged with the groove 356, there is enough clearance under the saddle 350 to pass the longitudinal member 322 of the first attachment portion 312 through the thru hole 334 of the second attachment portion 314.

Figure 12:
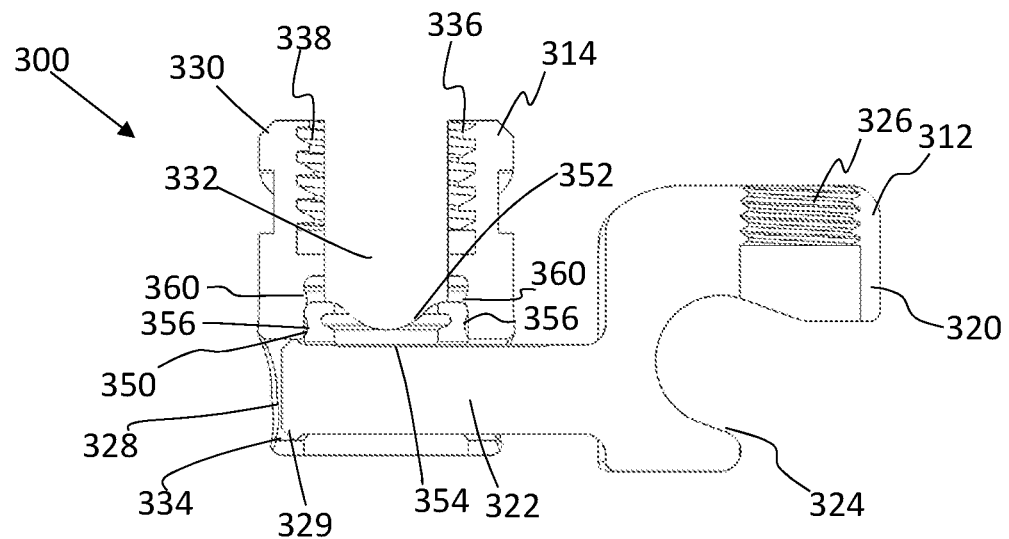
FIG. 12 is a cross-sectional view of the saddle component in the downward position, thereby preventing the first and second attachment portions from disassembling from one another.

After the longitudinal member 322 of the first attachment portion 312 is passed through, the saddle 350 of the second attachment portion 314 is pressed down below the modular bump 360 and/or the bump 360 is not engaged with the groove 356, as shown in FIG. 10. As best seen in FIGS. 10 and 12, the geometry of the second attachment portion 314 is such that the saddle 350 (located below the modular bump 360) blocks the distal end 328 of the longitudinal member 322 from passing back through the thru hole 334 of the second attachment portion 314, thus preventing disassembly. The geometry of the underside of the saddle 350 is such that the second attachment portion 314 can rotate about the longitudinal axis L of the longitudinal member 322 of the first attachment portion 312. The second attachment portion 314 is also able to translate along the length of the longitudinal member 322 of the first attachment portion 312. Thus, the second attachment portion 314 is able to rotate relative to the first attachment portion 312 such that an angle between the first and second rods 16 may be adjusted, and/or the second attachment portion 314 is able to translate relative to the first attachment portion 312 such that a distance between the first and second rods 16 may be adjusted. In some embodiments, the hole 334 may alternatively be a blind hole.

Turning now to FIGS. 13-17, an embodiment of an implant, connector assembly, or connector 400 is shown. Connector 400 is similar to connector 300 but the saddle is a top loaded modular saddle 450. Similar to connector 300, connector 400 includes a first attachment portion 412 with a body 420 having a recess 424 for receiving rod 16 and an opening 426 for receiving a securing member, such as a threaded cap 418 (shown in FIG. 17), to secure the first rod 16. The longitudinal member 422 extends to a free end 428, and the longitudinal member 422 is positionable within opening 434 in the body 430 of the second attachment portion 414. The second attachment portion 414 has a tulip shaped body 430 with first and second extensions 436, 438 separated by an opening 432 configured to receive the second rod 16. Similar to connector 200, the end 428 of the longitudinal member 422 may be an enlarged end 429.

The saddle 450 includes an upper surface defining a first slot 452 for receiving a portion of rod 16 and a lower surface defining a second slot 454 for receiving a portion of the longitudinal member 422. The saddle 450 is configured to be loaded in from the top of the second attachment portion 414. The saddle 450 may be elliptical in shape to keep the rod slot 452 oriented in alignment with the rod slot 432 of the second attachment portion 414 and the bottom slot 454 oriented with the thru hole 434 in the second attachment portion 414 configured to accept the longitudinal member 422.

Initially, the long axis of the ellipse is oriented within the rod slot 432 of the second attachment portion 414. The saddle 450 is then lowered into position and rotated 90° into a groove where the modular bump is located. As best seen in FIG. 14, the saddle 450 is located above the modular bump, such that there is enough clearance under the saddle 450 to pass the longitudinal member 422 of the first attachment portion 412 through the thru hole 434 of the second attachment portion 414. After the longitudinal member 422 of the first attachment portion 412 is passed, the saddle 450 of the second attachment portion 414 is pressed down below the modular bump. As best seen in FIG. 15, the geometry of the second attachment portion 414 is such that the saddle 450 (located below the modular bump) blocks the distal end 428 of the longitudinal member 422 from passing back through the thru hole 434 of the second attachment portion 414, thus preventing disassembly. The geometry of the underside of the saddle 450 allows for the second attachment portion 414 to rotate about the longitudinal axis L of the longitudinal member 422 of the first attachment portion 412. The second attachment portion 414 is also able to translate along the longitudinal member 422 of the first attachment portion 412. Thus, the second attachment portion 414 is able to rotate relative to the first attachment portion 412 such that an angle between the first and second rods 16 may be adjusted, and/or the second attachment portion 414 is able to translate relative to the first attachment portion 412 such that a distance between the first and second rods 16 may be adjusted. In some embodiments, the hole 434 may alternative be a blind hole.

With further emphasis on FIGS. 16-17, the design of the first attachment portion 412 may be an open style clamp. For example, the clamp body 420 may have a side facing and/or downward facing opening 424 configured to accept spinal rod 16. A securing member 418, such as a threaded set screw, may be used to secure the spinal rod 16 within the clamp body 420. The threaded set screw 418 may have one or more threads along an outer surface configured to mate with one or more corresponding threads within the opening 426. An opening in an upper surface of the threaded set screw 418 may be configured to receive an instrument, such as a screwdriver. Although a threaded securing member 418 is exemplified, it will be appreciated that non-threaded securing members, locking caps, or other suitable fasteners may be used. The open style clamp 420 has a longitudinal member 422 extending from the clamp body 420 as described herein. When the threaded set screw 418 is threaded downward through opening 426 and into contact with the spinal rod 16, the spinal rod 16 is thereby rigidly attached to the first attachment portion 412.

Figure 18:
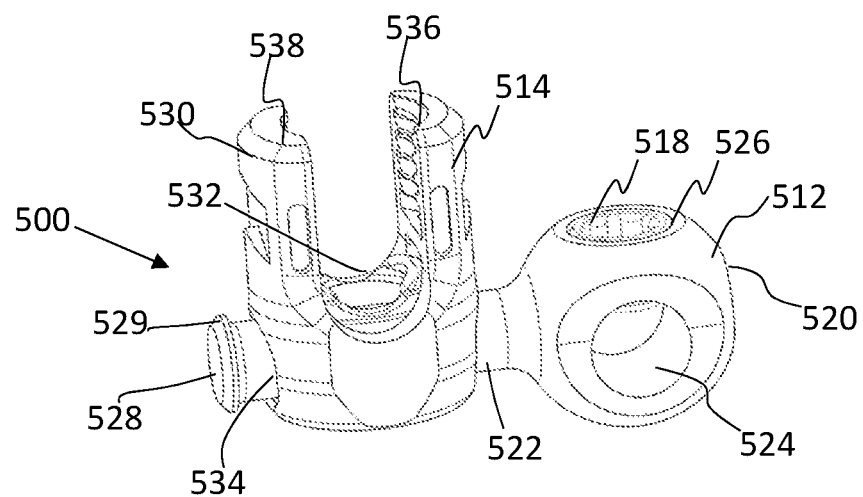
FIG. 18 is a perspective view of a connector according to one embodiment having a closed style clamp.
Figure 19:
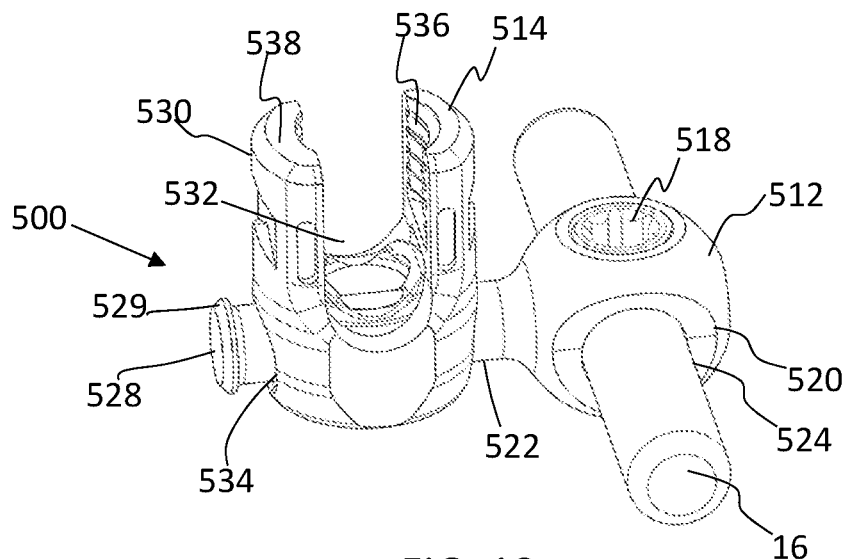
FIG. 19 shows the connector of FIG. 18 secured to a spinal rod.
Figure 20:
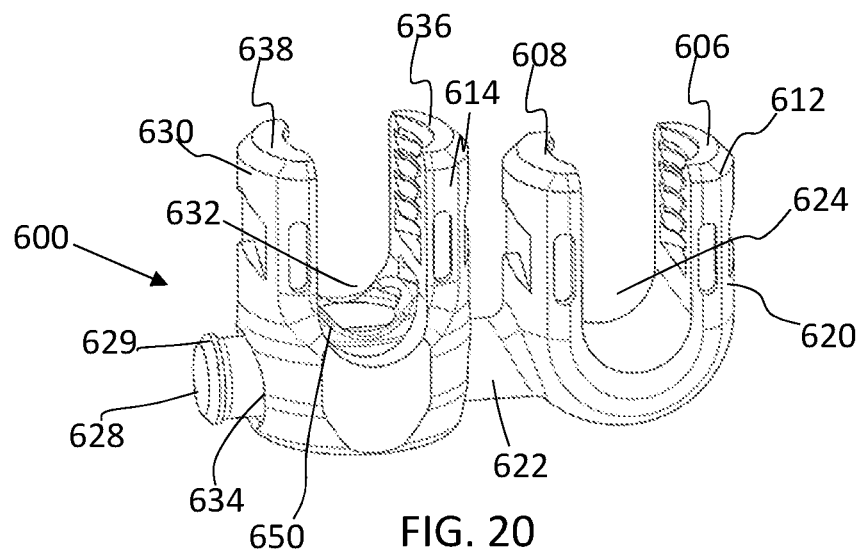
FIG. 20 is a perspective view of a connector according to another embodiment having a head style clamp.
Figure 21:
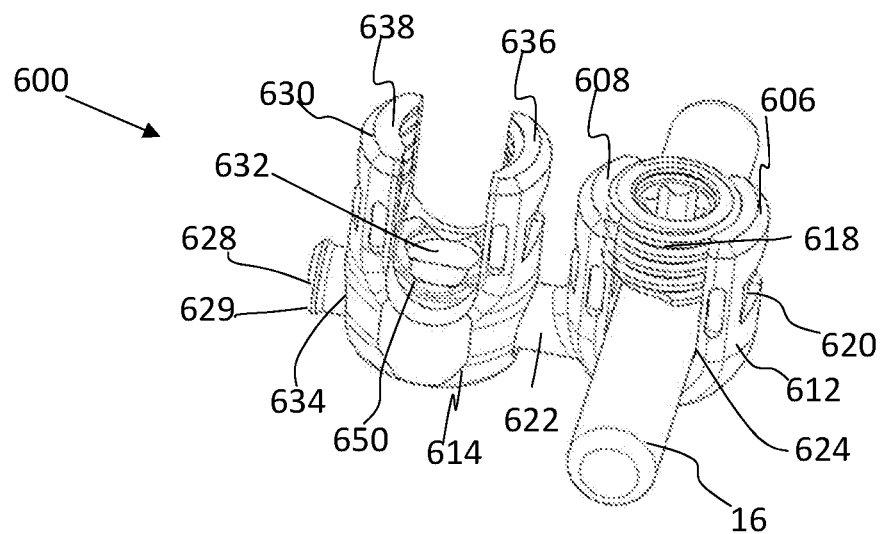
FIG. 21 shows the connector of FIG. 20 secured to a spinal rod.

Turning now to FIGS. 18-19, an alternative design of the first attachment portion 512 is shown as a closed style clamp. Connector 500 is similar to connector 10 but first attachment portion 512 has a closed body. Similar to connector 10, connector 500 includes a first attachment portion 512 with a longitudinal member 522 extending to a free end 528, and the longitudinal member 522 is positionable within opening 534 in the body 530 of the second attachment portion 514. The second attachment portion 514 has a tulip shaped body 530 with first and second extensions 536, 538 separated by an opening 532 configured to receive the second rod 16. Similar to connector 200, the end 528 of the longitudinal member 522 may be an enlarged end 529. In some embodiments, the opening 534 is a through hole extending from a first side of the body 530 to a second side opposite the first side. In some embodiments, the opening 534 may alternatively be a blind hole that extends from the first side of the body 530 and terminates at a point between the first side and the second side.

Unlike the open style clamp, the first attachment portion 512 has a closed style body 520 where the rod 16 is entirely surrounded by the body 520 of the first attachment portion 512. The closed clamp body 520 may have an opening 524 extending therethrough, which is configured to accept a first spinal rod 16. The closed clamp body 520 defines a second opening 526 configured to retain a securing member 518. The opening 526 may be in fluid communication with opening 524. The opening 526 may be oriented generally perpendicularly to opening 524 although other orientations may be used. The securing member 518, such as a threaded set screw, is configured to secure the spinal rod 16 within the closed body 520 of the first attachment portion 512. When the threaded set screw 518 is threaded downward through opening 526 and into contact with the spinal rod 16, the spinal rod 16 is thereby rigidly attached to the first attachment portion 512.

With reference to FIGS. 20-23, an alternative design of the first attachment portion 612 is shown as a head style clamp. Connector 600 is similar to connector 10 but first attachment portion 612 has a tulip shaped body 620. Similar to connector 10, connector 600 includes second attachment portion 614 with a tulip shaped body 630 with first and second extensions 636, 638 separated by an opening 632 configured to receive the second rod 16. Similar to connector 200, the end 628 of the longitudinal member 622 may be an enlarged end 629.

Unlike the open style clamp, the first attachment portion 612 has a head style clamp similar to the clamp body 630 of the second attachment portion 614. The first attachment portion 612 includes a tulip shaped body 620 with first and second extensions 606, 608 separated by an opening 624. The clamp body 620 has an upward facing rod slot 624 configured to accept the first spinal rod 16. The rod slot 624 may be at least partially threaded, for example, to accept a locking cap 618 for securing the spinal rod 16. The head style clamp 620 has a longitudinal member 622 extending from the clamp 620 as described in other embodiments.

The second attachment portion 614 also includes a head style clamp. The clamp body 630 has an upward facing rod slot 632 configured to accept the second spinal rod 16. The rod slot 632 may be at least partially threaded, for example, to accept a locking cap 618 for securing the second spinal rod 16. The clamp 630 may have a saddle 650, which may be loaded from the top (e.g., as shown in FIGS. 13-15) or bottom (e.g., as shown in FIGS. 8-12). The saddle 650 is able to translate within the head style clamp 630 such that when a locking cap 618 is threaded into the clamp 630, the locking cap 618 forces the spinal rod 16 to contact the saddle 650, which forces the saddle 650 to then contact the longitudinal member 622 of the first attachment portion 612, thereby securing the construct. The force of the saddle 650 on the longitudinal member 622 of the first attachment portion 612 locks the translation and/or rotation of the second attachment portion 614 with respect to the first attachment portion 612.

Figure 24:
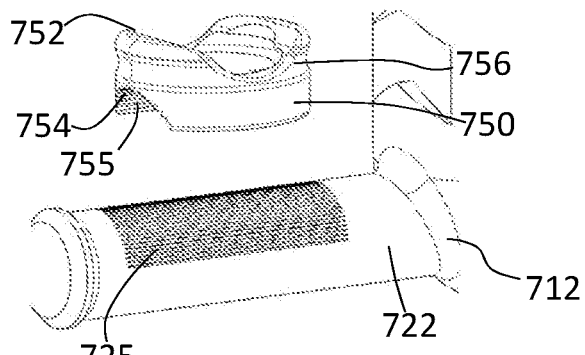
FIG. 24 depicts an embodiment of the saddle having a grooved surface that mates with a grooved surface on the longitudinal member of the first attachment portion.

Turning now to FIG. 24, an embodiment of a saddle 750 is shown where the bottom surface 754 of the saddle 750 has one or more grooves 755 that are configured to mate with matching grooves 725 on the longitudinal member 722 of the first attachment portion 712. Similar to bottom loading saddle 350, saddle 750 has an upper surface defining a first slot 752 for receiving a portion of rod 16 and a lower surface defining a second slot 754 for receiving a portion of the longitudinal member 722. The saddle 750 defines a recess or groove 756 along an outer surface of the saddle 750 configured to engage with a bump, such as modular bump 360, within the second attachment portion. The grooves 725, 755 may include ridges, serrations or other surface roughening configured to enhance friction between the saddle 750 and longitudinal member 722. The grooves 755 may cover the entire slot 754 in the bottom surface of the saddle 750 or a portion thereof. Similarly, the grooves 725 may cover a portion of the longitudinal member 722 (e.g., an upper portion) or the entire outer surface of the longitudinal member 722. The mating grooves 725, 755 engage when the locking cap presses the rod 16 into the saddle 750, adding additional locking force to prevent translation and/or rotation of the second attachment portion along the longitudinal member 722 of the first attachment portion 712. It is envisioned that such surface roughening or grooves may be added to any of the embodiments described herein.

Figures 25, 26:
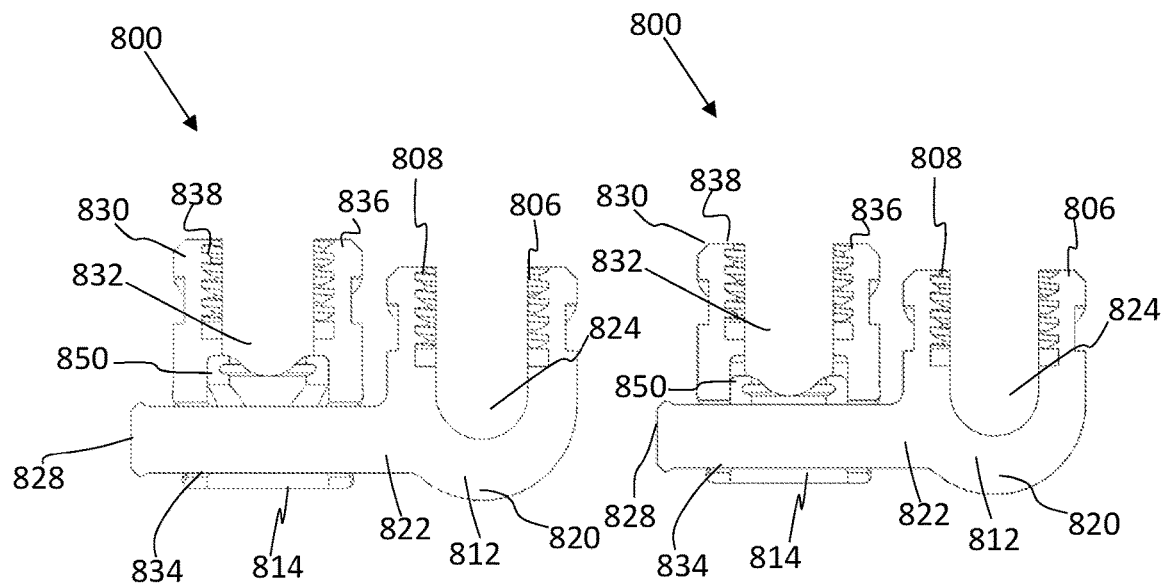
FIG. 25 is a cross-sectional view of a connector having a bottom loaded saddle in an upward position, thereby allowing the first and second attachment portions to move relative to one another.
FIG. 26 is a cross-sectional view of the connector of FIG. 25 with the saddle in a downward position, thereby locking the relative positions of the first and second attachment portions.

Turning now to FIGS. 25 and 26, an embodiment of a translating bottom loaded saddle 850 not constrained by a modular bump is shown. Connector 800 is similar to bottom loading connector 600 where the first attachment portion 812 has a tulip shaped body 820 with first and second extensions 806, 808 separated by a top facing opening 824 configured to receive the first rod 16, and the second attachment portion 814 has a tulip shaped body 830 with first and second extensions 836, 838 separated by a top facing opening 832 configured to receive the second rod 16. The longitudinal member 822 of the first attachment member 812 terminates at free end 828 and the longitudinal member 822 extends through an opening 834 in the body 830 of the second attachment member 814 to allow rotation and/or translation of the second attachment member 814.

In this embodiment, the bottom loaded saddle 850 is loaded similar to saddle 350 shown in FIG. 8. However, without the constraint of a modular bump, the bottom loaded saddle 850 is free to translate within the internal cavity of the second attachment portion 814. Thus, as shown for the connector 800 of FIG. 25, the saddle 850 is free to translate upward, thereby allowing for passage of longitudinal member 822 though opening 834. In FIG. 26, the saddle 850 is free to translate downward within the second attachment portion 814, thereby locking the longitudinal member 822. In some embodiments, the opening 834 is a through hole extending from a first side of the body 830 to a second side opposite the first side. In some embodiments, the opening 834 may alternatively be a blind hole that extends from the first side of the body 830 and terminates at a point between the first side and the second side.

Figures 27, 28:
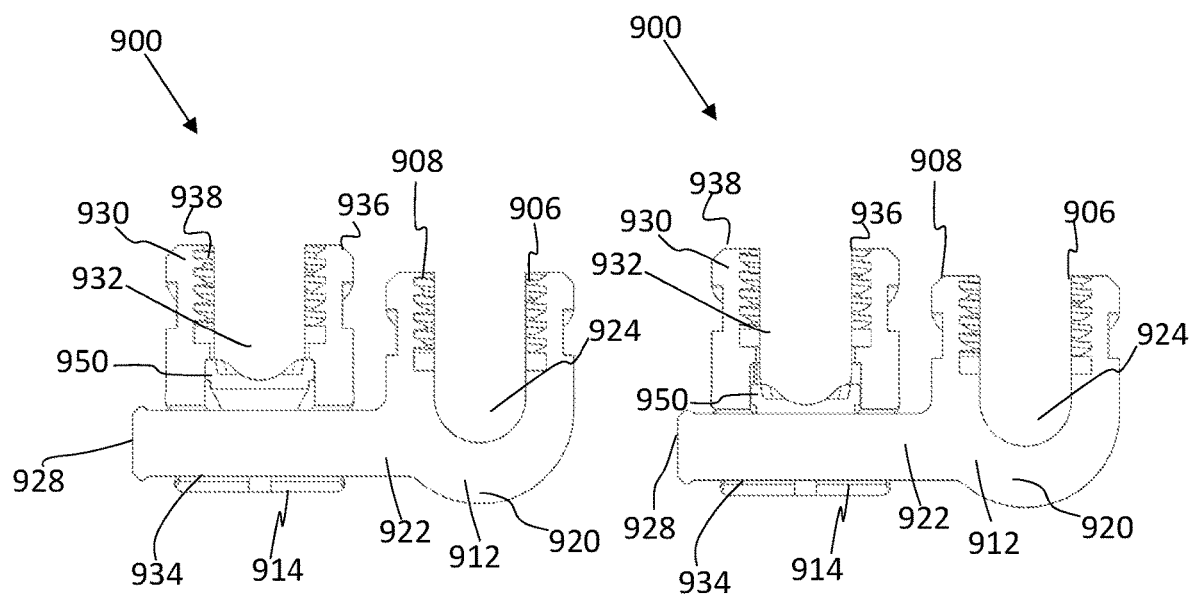
FIG. 27 is a cross-section view of a connector having a top loaded saddle in an upward position, thereby allowing the first and second attachment portions to move relative to one another.
FIG. 28 is a cross-sectional view of the connector of FIG. 27 with the saddle in a downward position, thereby locking the relative positions of the first and second attachment portions.

With emphasis on FIGS. 27 and 28, an embodiment of a translating top loading saddle 950 not constrained by a modular bump is shown. Connector 900 is similar to connector 600 where the first attachment portion 912 has a tulip shaped body 920 with first and second extensions 906, 908 separated by a top facing opening 924 configured to receive the first rod 16, and the second attachment portion 914 has a tulip shaped body 930 with first and second extensions 936, 938 separated by a top facing opening 932 configured to receive the second rod 16. The longitudinal member 922 of the first attachment member 912 terminates at free end 928 and the longitudinal member 922 extends through an opening 934 in the body 930 of the second attachment member 914 to allow rotation and/or translation of the second attachment member 914. In some embodiments, the opening 934 is a through hole extending from a first side of the body 930 to a second side opposite the first side. In some embodiments, the opening 934 may alternatively be a blind hole that extends from the first side of the body 930 and terminates at a point between the first side and the second side.

Similar to saddle 850, the saddle 950 is free to translate within the internal cavity of the body 930 of the second attachment portion 914. Thus, as shown in the connector 900 of FIG. 27, the saddle 950 is free to translate up, and in FIG. 28, the saddle 950 is free to translate down within the second attachment portion 914. Thus, in the upward, unlocked position, the second attachment portion 914 is able to rotate relative to the first attachment portion 912 such that an angle between the first and second rods 16 may be adjusted, and/or the second attachment portion 914 is able to translate relative to the first attachment portion 912 such that a distance between the first and second rods 16 may be adjusted. In the downward, locked position, the location and orientation of the second attachment portion 914 is fixed relative to the first attachment portion 912.

Turning now to FIGS. 29-35, an implant, connector assembly, or connector 1000 is shown with a ball joint component 1070. Connector 1000 is similar to connector 600 where the first attachment portion 1012 has a tulip shaped body 1020 with first and second extensions 1006, 1008 separated by a top facing opening 1024 configured to receive the first rod 16, and the second attachment portion 1014 has a tulip shaped body 1030 with first and second extensions 1036, 1038 separated by a top facing opening 1032 configured to receive the second rod 16. The longitudinal member 1022 of the first attachment member 1012 terminates at free end 1028 and the longitudinal member 1022 extends through an opening 1034 in the body 1030 of the second attachment member 1014. In some embodiments, the opening 1034 is a through hole extending from a first side of the body 1030 to a second side opposite the first side. In some embodiments, the opening 1034 may alternatively be a blind hole that extends from the first side of the body 1030 and terminates at a point between the first side and the second side.

Figure 29:
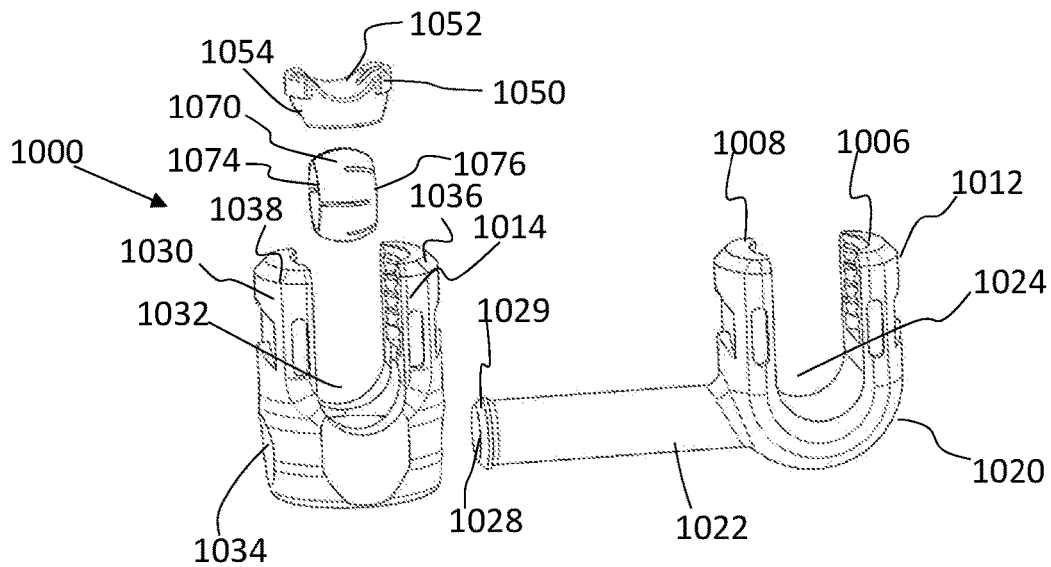
FIG. 29 is an exploded view of a connector according to one embodiment having a ball joint.

As seen in the exploded view of FIG. 29, the second attachment portion 1014 is configured to receive a saddle 1050 and a ball joint 1070. The saddle includes an upper surface defining a first slot 1052 configured for receiving a portion of rod 16 and a lower surface defining a second slot 1054 configured for receiving a portion of the ball joint 1070. The saddle 1050 may have one or more protrusions, for example, around an upper periphery of the saddle 1050. Saddle 1050 may have similar features to the other saddles described herein.

Figure 30:
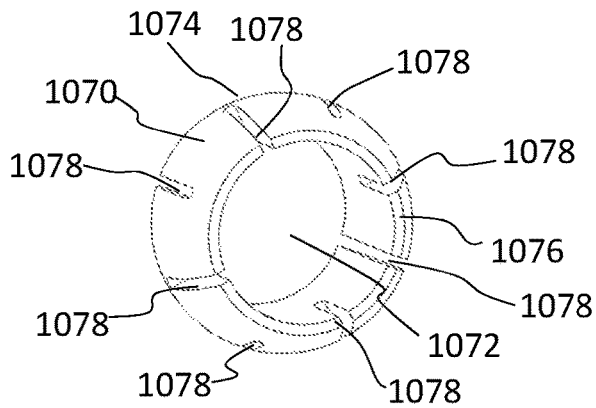
FIG. 30 is a perspective view of the spherical joint component of the ball joint of FIG. 29.
Figure 31:
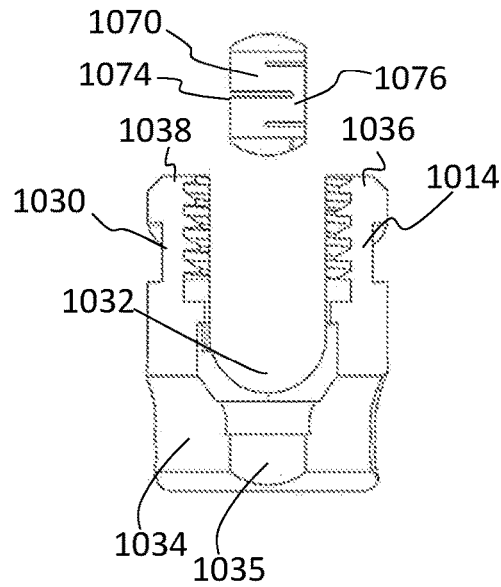
FIG. 31 is an exploded view of the head style clamp with a spherical recess and a spherical joint component.
Figure 32:
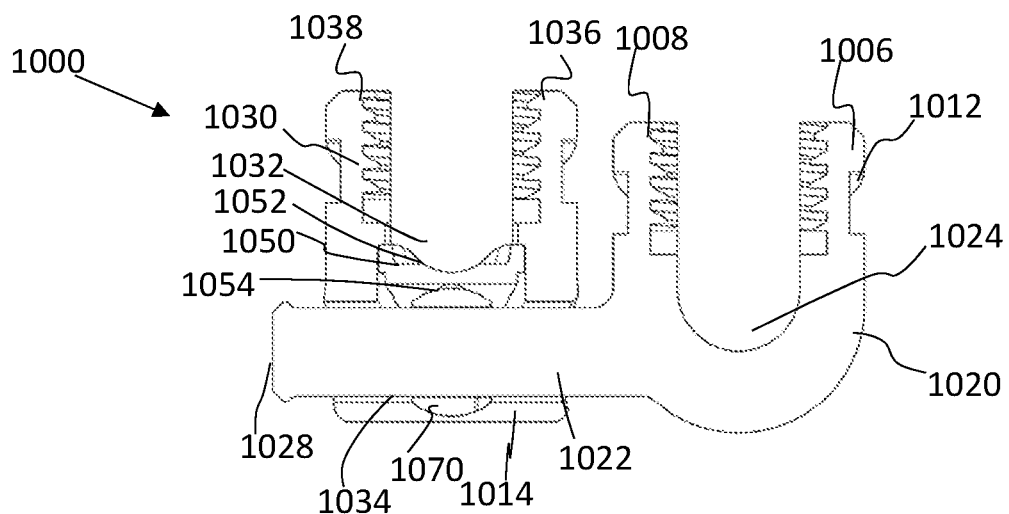
FIG. 32 is a cross-sectional view of the assembled connector of FIG. 29.

With emphasis on FIG. 30, the ball joint 1070 extends from a first end 1074 to a second end 1076 and may generally form a ring shape. A thru hole 1072 extends centrally between the first and second ends 1074, 1076, and the thru hole 1072 is configured to accept the longitudinal member 1022 of the first attachment portion 1012. The outer surface of the ball joint 1070 may be curved or generally spherical between the first and second ends 1074, 1076. One or more slits 1078 may be provided through the ball joint 1070, for example, to allow expansion and compression around the longitudinal member 1022. The slits 1078 may extend partially or fully through the body of the ball joint 1070. For example, at least one slit 1078 may extend completely through the ball joint 1070, such that the ball joint 1070 forms a split ring. The ball joint 1070 may be split so that it can expand to accept the larger distal end 1029 of the longitudinal member 1022. In the embodiment shown, in addition to the split ring, a plurality of partial linear slits 1078 extend inwardly from the first end 1074 and a plurality of partial linear slits 1078 extend inwardly from the second end 1076 in an alternating fashion. The ball joint 1070 may be configured with any suitable number, shape, and type of slits or other feature to allow for compression around the longitudinal member 1022.

Figure 35:
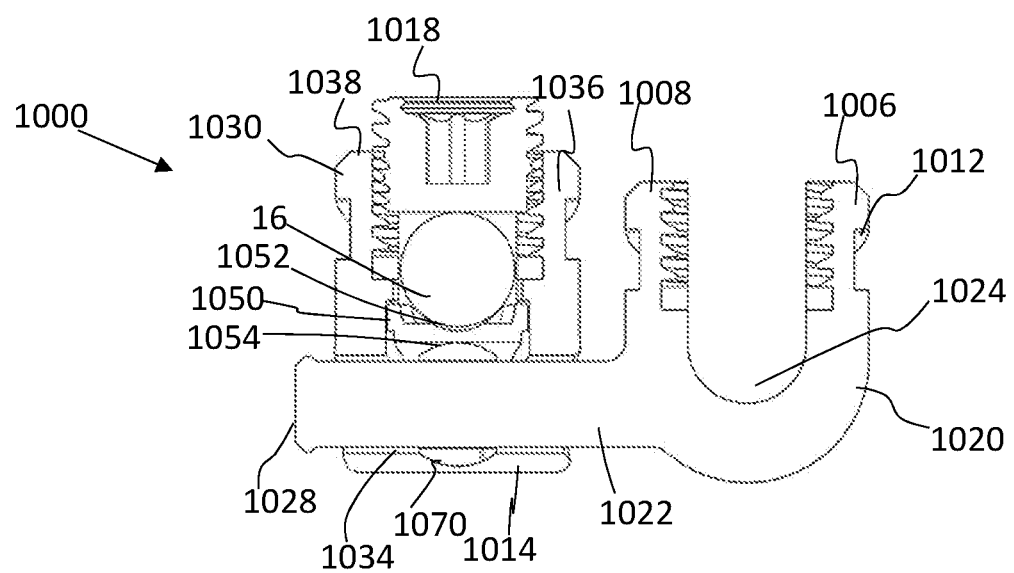
FIG. 35 is a cross-section view of the assembled connector of FIG. 29 with the locking cap securing a spinal rod and saddle, and thereby locking the construct.

The main body 1030 of the second attachment portion 1014 may have a spherical recess 1035 configured to accept at least a portion of the ball joint 1070. The saddle 1050 has a spherical recess 1054 on the bottom surface of the saddle 1050 to engage the ball joint 1070. The saddle 1050 may be top loaded. As best seen in FIG. 35, the second attachment portion 1014 may have a thread to accept a securing member, such as a threaded locking cap 1018. The saddle 1050 is able to translate within the head style clamp 1030 such that when the locking cap 1018 is threaded into the clamp 1030, the locking cap 1018 forces the spinal rod 16 to contact the saddle 1050, which forces the saddle 1050 to then contact the spherical joint 1070 to secure the construct. The force of the saddle 1050 on the spherical joint 1070 locks the translation, rotation, wag, and/or tilt of the second attachment portion 1014 with respect to the first attachment portion 1012.

Figure 33:
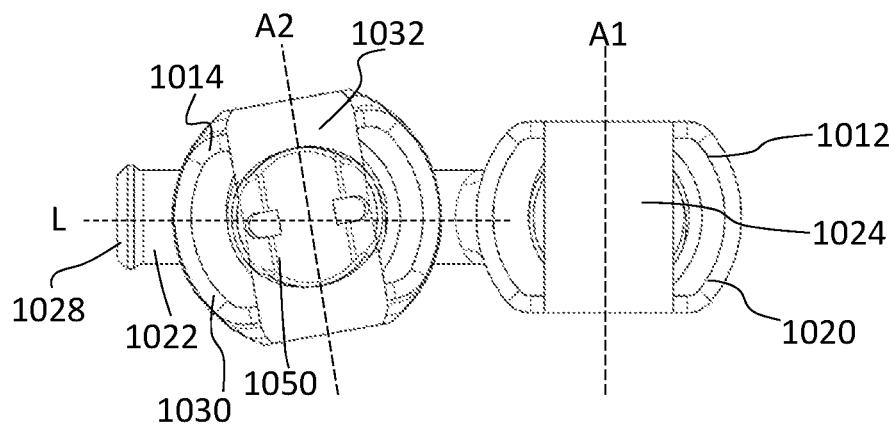
FIG. 33 is a top view of the connector of FIG. 29 with an angled second attachment portion.

The ball joint 1070 and saddle 1050 configuration allows the second attachment portion 1014 to translate, rotate, wag, and tilt with respect to the first attachment portion 1012. As best seen in FIG. 33 from a top-down perspective, the second attachment portion 1014 is able to wag relative to the first attachment portion 1012. The first rod 16 may be oriented along axis A1 through rod slot 1024 in the first attachment portion 1012, and the second rod 16 may be oriented along axis A2 through rod slot 1032 in the second attachment portion 1014. While axis A1 may be fixed, axis A2 is able to be angled relative to A1. Thus, axis A2 may be generally parallel, acute, or obtuse relative to axis A1.

Figure 34:
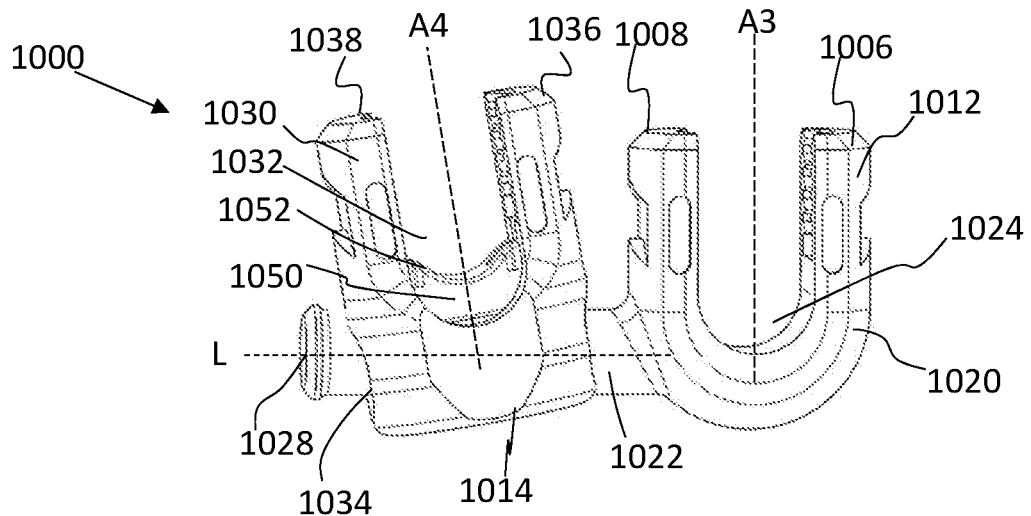
FIG. 34 is a side view of the connector of FIG. 29 with a tilted second attachment portion.

As best seen in FIG. 34 from a side perspective, the second attachment portion 1014 is also able to tilt relative to the first attachment portion 1012. The body 1020 of the first attachment portion 1012 may be oriented along a vertical axis A3 for rod slot 1024, and the body 1030 of the second attachment portion 1014 may be oriented along a vertical axis A4 for rod slot 1032. While axis A3 may be fixed, axis A4 is able to be angled relative to A3, thereby permitting the top of the second attachment portion 1014 to tilt toward or away from the first attachment portion 1012. Once fixed in position, axis A4 may be generally parallel, acute, or obtuse relative to axis A3. Thus, the second attachment portion 1014 is configured to translate, rotate, wag, and/or tilt to position the first and second rods 16 in their optimal positions and orientations.

Turning now to FIGS. 36-40, an implant, connector assembly, or connector 1100 is shown with an anchored ball joint component 1170. Connector 1100 is similar to connector 1000 where the first attachment portion 1112 has a tulip shaped body 1120 with first and second extensions 1106, 1108 separated by a top facing opening 1124 configured to receive the first rod 16, and the second attachment portion 1114 has a tulip shaped body 1130 with first and second extensions 1136, 1138 separated by a top facing opening 1132 configured to receive the second rod 16. The longitudinal member 1122 of the first attachment member 1112 terminates at free end 1128 and may have an enlarged end 1129. The longitudinal member 1122 is configured to extend through opening 1134 in the body 1130 of the second attachment member 1114. The second attachment portion 1114 is configured to receive a saddle 1150 (the same or similar to saddle 1050) and a ball joint 1170, which operates in a manner similar to connector 1000. In some embodiments, the opening 1134 is a through hole extending from a first side of the body 1130 to a second side opposite the first side. In some embodiments, the opening 1134 may alternatively be a blind hole that extends from the first side of the body 1130 and terminates at a point between the first side and the second side.

In this embodiment, the ball joint 1170 is anchored to the longitudinal member 1122. As best seen in FIG. 37, the ball joint 1170 is similar to ball joint 1070 but further has a slot 1180 that accepts a mating ring 1182 on the longitudinal member 1122 of the first attachment portion 1112. The mating ring 1182 may be a partial or continuous protrusion, bump, or other feature extending around the circumference of the longitudinal member 1122. The ring 1182 may be positioned along the length of the longitudinal member 1122 between the body 1120 and the free end 1128. For example, the ring 1182 may be generally centrally located along the length of the longitudinal member 1122. The slot 1180 may be a slot, recess, or groove configured to receive at least a portion of the ring 1182. For example, the slot 1180 may be an elongate linear slot having a length greater than its width W1. The mating connection 1180, 1182 is configured to keep the ball joint 1170 anchored along the longitudinal member 1122.

Figure 39:
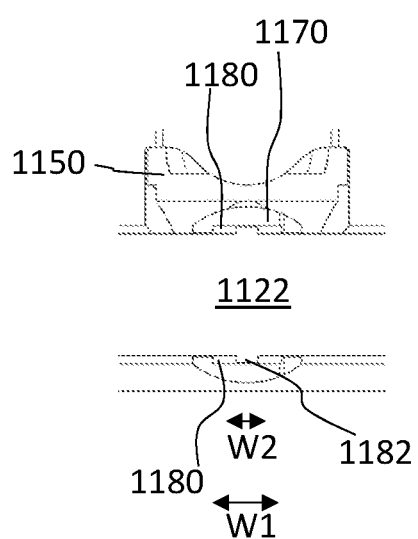
FIG. 39 is a close-up cross-section view of the spherical joint component according to one embodiment.
Figure 40:
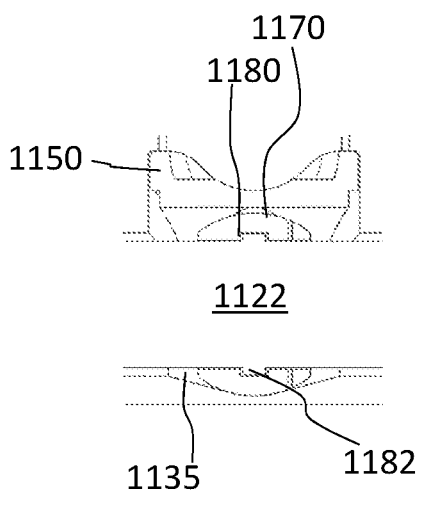
FIG. 40 is a close-up cross-section view of the spherical joint component according to another embodiment.

With the anchored ball joint 1170, translation between the first and second attachment portions 1112, 1114 may be achieved in a number of ways. As best seen in FIG. 39, translation between the first and second attachment portions 1112, 1114 can be accommodated by making the width W1 of the slot 1180 in the spherical joint 1170 longer or wider than the width W2 of the ring 1182 on the longitudinal member 1122. Thus, the ring 1182 is able to translate along the width W1 of the slot 1180 to thereby translate the second attachment portion 1114 relative to the first attachment portion 1112. Alternatively or additionally, the translation can be accommodated by making the size of the spherical recess 1135 within the body 1130 of the second attachment portion 1114 greater than the overall size of the spherical joint 1170. As best seen in FIG. 40, the spherical recess 1135 is larger than the outer dimensions of the spherical joint 1170, thus allowing the spherical joint 1170 (in which the first attachment portion 1112 may be anchored) to translate within the body 1130 of the second attachment portion 1114. Thus, even with an anchored ball joint 1170, translation may be permitted and the amount of translation may be controlled and/or limited by the relative widths W1, W2 and/or dimensions of the recess 1135 and joint 1170. The ball joint 1170 also permits rotation, wag, and/or tilt in the ways described for connector 1000.

Turning now to FIGS. 41-45, an implant, connector assembly, or connector 1200 is shown with a wagging saddle 1250. Connector 1200 is similar to connector 1100 where the first attachment portion 1212 has a tulip shaped body 1220 with first and second extensions 1206, 1208 separated by a top facing opening 1224 configured to receive the first rod 16. The longitudinal member 1222 of the first attachment member 1212 terminates at free end 1228, may have an enlarged end 1229, and may have an anchoring ring 1282 (the same or similar to ring 1182). The second attachment portion may be the same or similar to second attachment portion 1114 or may include any of the features of the second attachment portions described herein.

Figure 41:
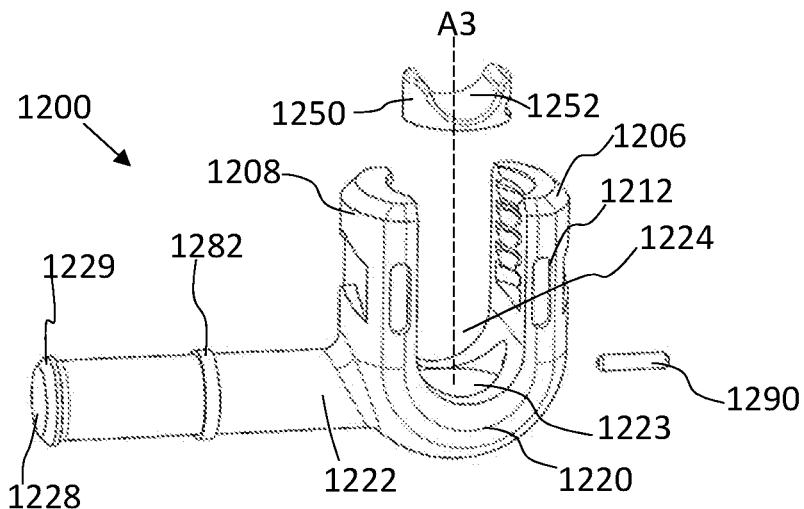
FIG. 41 is an exploded perspective view of a first attachment portion according to one embodiment having a wagging saddle and a pin.
Figure 42:
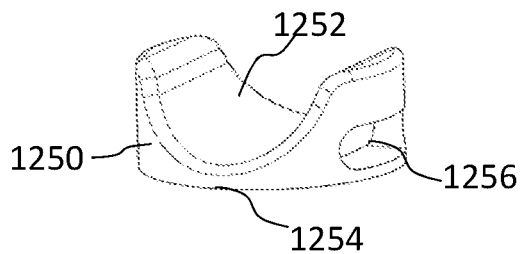
FIG. 42 shows a close-up view of the saddle of FIG. 41.
Figure 43:
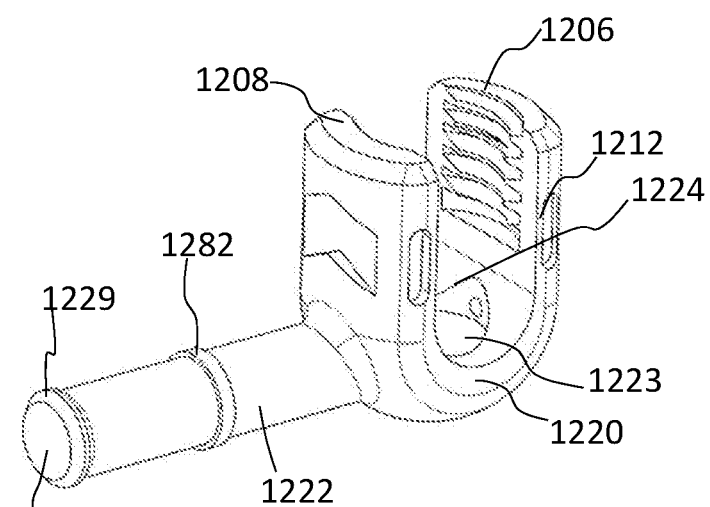
FIG. 43 shows a perspective view of the first attachment portion of FIG. 41.
Figure 44:
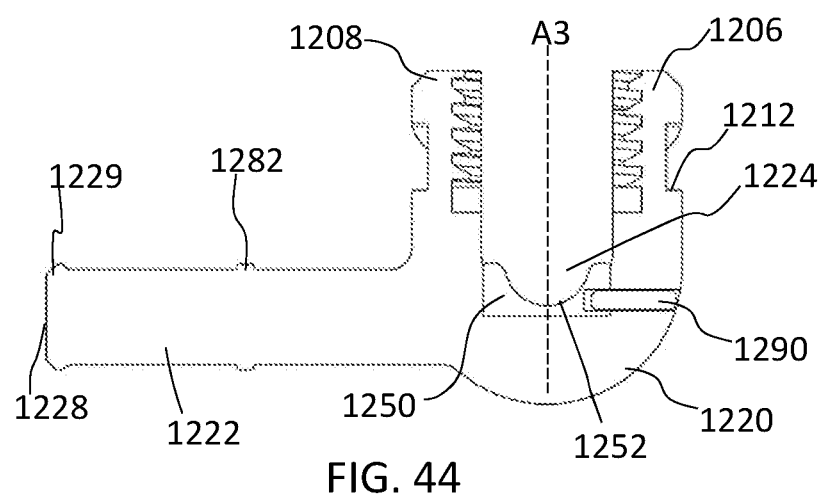
FIG. 44 is a cross-section view of the first attachment portion of FIG. 41 with wagging saddle and pin.

As best seen in FIG. 41, the saddle 1250 sits in a recess 1223 at the base of the rod slot 1224 of body 1220 of the first attachment portion 1212. The saddle 1250 may be retained by a retention member 1290, such as a pin, tab, peening, adhesive or other securing mechanism. With emphasis on FIG. 42, the saddle 1250 includes an upper surface defining a contoured or curved slot 1252 configured for receiving a portion of rod 16 and a lower surface 1254. The lower surface 1254 may be curved, flat or otherwise configured to mate with the body 1220 of the first attachment portion 1212. A side surface of the saddle 1250 has one or more grooves 1256 in which the retention member 1290 is received. The groove 1256 may be an elongate channel, for example. The pin 1290 is able to slide within the groove 1256 to guide movement of the saddle 1250. Thus, the saddle 1250 is able to rotate about the vertical axis A3 of the head style attachment portion 1212.

Figure 45:
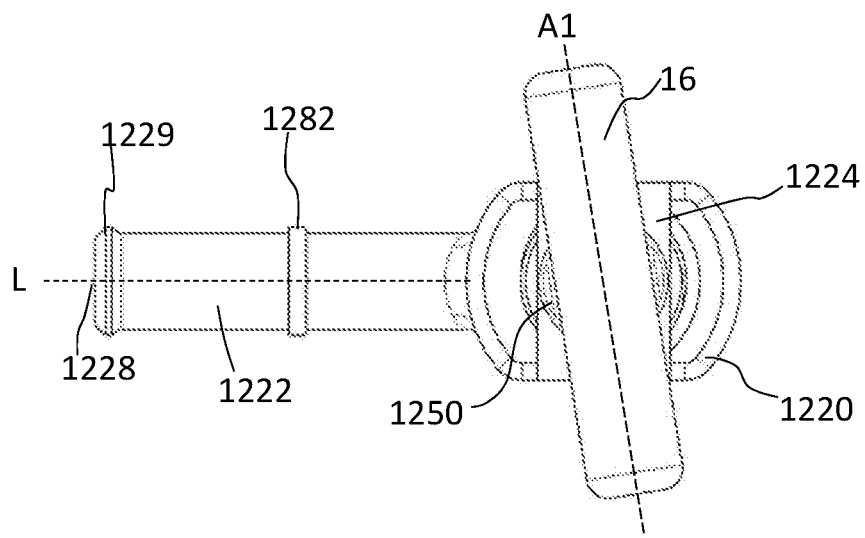
FIG. 45 is a top view of a spinal rod positioned within the first attachment portion and angled therein.

The rotation of the saddle 1250 is locked when a locking cap (such as threaded securing member 618 shown in FIG. 21) is threaded down and applies axial force onto the rod 16. This allows the rod 16 to enter the rod slot 1224 at varying angles in order to increase the ease of rod placement and construct connection. As best seen in FIG. 45, the rod 16 is positioned angled in the rod slot 1224 of the head style clamp 1212. In other words, the longitudinal axis A1 for the rod 16 is no longer fixed (perpendicular to the longitudinal axis L of the longitudinal member 1222 as shown in FIG. 33) but is independently adjustable. Thus, both the angle of the first rod 16 in saddle 1250 in the first attachment portion 1212 and the angle of the second rod 16 in the second attachment portion may each be independently adjusted to achieve the desired rod placement.

The connectors described herein may improve the ease of surgeons in attaching instrumentation to existing spinal rod constructs. Spinal connector implants that offer the ability to translate and/or rotate may save operating time, cause less disruption to the patient, and/or could minimize patient recovery time. Oftentimes differences in the trajectory and location between new pedicle screws and the existing instrumentation make connecting the two segments difficult. Static connectors require the surgeon to bend the new rod into a specific shape to extend fixation from the connector implant to the new pedicle screws. Connector implants that can translate, rotate, wag, and/or tilt allow for more options for the surgeon to place the rod and therefore does not require the surgeon to make precise bends in order for the connection to work. Therefore, connectors that are able to translate, rotate, wag, and/or tilt offer a unique advantage during revision surgeries when there is a need to extend fixation to adjacent spinal levels.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A connector system comprising:
   a first threaded locking cap;
   a first attachment portion having a first body portion configured to receive and secure a first spinal rod, the first body portion having a curved closed bottom portion and an open upper end for receiving the first spinal rod and threadingly receiving the first threaded locking cap to lock the first spinal rod to the first body portion, the first attachment portion having a longitudinal member extending from the first body portion and terminating at a free end;
   a second attachment portion having a second body portion configured to receive and secure a second spinal rod, the second attachment portion having an opening extending therethrough, the longitudinal member of the first attachment portion is received through the opening of the second attachment portion, and wherein the second attachment portion is able to translate along the longitudinal member and rotate about the longitudinal member of the first attachment portion; and
   a ball joint in the form of a single ring disposed in the second attachment portion and configured to receive the longitudinal member.

2. The system of claim 1, wherein the free end of the longitudinal member is enlarged such that the second attachment portion is unable to be disassembled from the first attachment portion.

3. The system of claim 1, wherein the second attachment portion further includes a saddle having an upper surface and a lower surface, the upper surface is configured to contact the second spinal rod, and the lower surface is configured to contact the longitudinal member of the first attachment portion.

4. The system of claim 3, wherein the saddle is top loaded.

5. The system of claim 1, wherein the first attachment portion is a u-shaped tulip-style connector.

6. A connector system comprising:
   a first threaded locking cap;
   a first attachment portion having a first body portion configured to receive and secure a first spinal rod, the first body portion having a curved closed bottom portion and an open upper end for receiving the first spinal rod and threadingly receiving the first threaded locking cap to lock the first spinal rod to the first body portion, the closed portion preventing any bone fastener to be attached to the first body portion, the first attachment portion having a longitudinal member extending from the first body portion and terminating at a free end;
   a second attachment portion having a second body portion configured to receive and secure a second spinal rod, the second attachment portion having an opening extending therethrough;
   a ball joint receivable within the opening of the second attachment portion, wherein the ball joint is a single ring; and
   a saddle having an upper surface configured to receive a portion of the second spinal rod and a lower surface configured to contact the ball joint,
   wherein the longitudinal member of the first attachment portion is received through the ball joint, and wherein the second attachment portion is able to translate, rotate, wag, and tilt about the longitudinal member of the first attachment portion.

7. The system of claim 6, wherein the ball joint has a spherical outer surface.

8. The system of claim 6, wherein the ball joint defines a plurality of slits configured to expand and contract about the longitudinal member.

9. A revision system comprising:
   a first threaded locking cap;
   a first spinal rod and a second spinal rod;
   a first attachment portion having a first body portion configured to receive and secure the first spinal rod, the first body portion having a curved closed bottom portion and an open upper end for receiving the first spinal rod and threadingly receiving the first threaded locking cap to lock the first spinal rod to the first body portion, the first attachment portion having a longitudinal member extending from the first body portion and terminating at a free end;
   a second attachment portion having a second body portion configured to receive and secure the second spinal rod, the second attachment portion having an opening extending therethrough;
   a ball joint receivable within the opening of the second attachment portion, wherein the ball joint is a single ring; and a saddle having an upper surface configured to receive a portion of the second spinal rod and a lower surface configured to contact the ball joint, wherein the longitudinal member of the first attachment portion is received through the ball joint, and wherein the second attachment portion is able to translate, rotate, wag, and tilt about the longitudinal member of the first attachment portion, and wherein when a locking member is secured to the second attachment portion, a downward force is applied to the saddle, which applies a force to the ball joint, thereby locking the position of the second attachment portion relative to the first attachment portion.

10. The system of claim 9, wherein one of the first or second spinal rods is a new spinal rod being implanted in a revision procedure.

* * * * *